(12) United States Patent
Boardman et al.

(10) Patent No.: US 12,280,200 B2
(45) Date of Patent: Apr. 22, 2025

(54) PORTABLE SUCTION SYSTEM

(71) Applicant: AIRO, LLC, Cheyenne, WY (US)

(72) Inventors: Jeff Boardman, Missoula, MT (US);
Scott Rendel, Missoula, MT (US);
Daniel Sharp, Missoula, MT (US)

(73) Assignee: AIRO, LLC, Cheyenne, WY (US)

( * ) Notice: Subject to any disclaimer, the term of this patent is extended or adjusted under 35 U.S.C. 154(b) by 0 days.

(21) Appl. No.: 18/381,754

(22) Filed: Oct. 19, 2023

(65) Prior Publication Data

US 2024/0131246 A1 Apr. 25, 2024
US 2024/0226412 A9 Jul. 11, 2024

Related U.S. Application Data

(60) Provisional application No. 63/417,406, filed on Oct. 19, 2022.

(51) Int. Cl.
*A61M 1/00* (2006.01)

(52) U.S. Cl.
CPC ............... *A61M 1/80* (2021.05); *A61M 1/91* (2021.05)

(58) Field of Classification Search
CPC ...... A61M 1/06; A61M 1/06935; A61M 1/80; A61M 1/75; A61M 1/604; A61M 1/74; A61M 1/742; A61M 1/743; A61M 1/81; A61M 2202/0014; A61M 1/815; A61M 1/918; A61M 1/90; A61M 1/96; A61M 1/962; A61M 1/964; A61M 1/966; A61M 1/984; A61M 27/00; B65B 31/04; B65B 31/06; B65B 31/047; F04D 17/168
See application file for complete search history.

(56) References Cited

U.S. PATENT DOCUMENTS

| | | | |
|---|---|---|---|
| 4,179,862 A * | 12/1979 | Landolt | B65B 31/024 53/512 |
| 4,747,424 A * | 5/1988 | Chapman | B66F 11/048 137/868 |
| 5,094,260 A * | 3/1992 | Stuart | G05D 16/2053 137/596.17 |
| 5,228,274 A * | 7/1993 | De Man | B65B 31/046 53/88 |

(Continued)

FOREIGN PATENT DOCUMENTS

WO 2009016603 A2 2/2009

OTHER PUBLICATIONS

International Searching Authority, International Search Report and Written Opinion for International Application No. PCT/US23/35482, mailed Apr. 15, 2024.

*Primary Examiner* — Scott J Medway
(74) *Attorney, Agent, or Firm* — Casimir Jones, S.C.; Brian F. Bradley

(57) ABSTRACT

A portable suction system including a pump device and a removable bag device. The pump device includes a housing defining a recess; a motor assembly positioned within the housing; a first rod at least partially extending from the housing into the recess; and a second rod at least partially extending from the housing into the recess. The first rod and the second rod are driven in response to energization of the motor assembly. The bag device is at least partially positioned within the recess, and the bag device includes: a bag; a vacuum connector; a first piston coupled to the first rod; and a second piston coupled to the second rod.

22 Claims, 21 Drawing Sheets

(56) References Cited

U.S. PATENT DOCUMENTS

| | | | | |
|---|---|---|---|---|
| 5,682,727 | A * | 11/1997 | Harte | B65B 31/024 53/512 |
| 5,765,608 | A * | 6/1998 | Kristen | B65B 31/047 141/96 |
| 5,795,328 | A * | 8/1998 | Barnitz | G05D 16/208 604/67 |
| 5,810,772 | A * | 9/1998 | Niederberger | A61M 1/06935 604/74 |
| 5,961,291 | A * | 10/1999 | Sakagami | F04D 29/70 417/42 |
| 6,220,299 | B1 * | 4/2001 | Arvidsson | F16K 11/052 137/329.05 |
| 6,319,410 | B1 * | 11/2001 | Allington | G01N 30/28 417/415 |
| 6,355,012 | B1 * | 3/2002 | Nuesch | A61M 1/06 604/74 |
| 7,003,928 | B2 * | 2/2006 | Patterson | B65B 51/146 53/434 |
| 7,569,031 | B2 * | 8/2009 | Britto | A61M 1/06 604/74 |
| 7,937,914 | B2 * | 5/2011 | Savicki | F01C 13/00 53/434 |
| 8,096,329 | B2 * | 1/2012 | Thuot | B65B 31/04 417/415 |
| 10,508,751 | B2 * | 12/2019 | Neal | F16K 11/022 |
| 11,047,501 | B2 * | 6/2021 | Leeseberg | F16K 31/0682 |
| 2004/0211792 | A1 * | 10/2004 | Vitantonio | B05B 9/0861 222/333 |
| 2005/0061813 | A1 * | 3/2005 | Vilalta | B65D 81/2015 220/212 |
| 2007/0055209 | A1 * | 3/2007 | Patel | A61P 31/04 604/315 |
| 2011/0140018 | A1 * | 6/2011 | Wei | F16K 31/06 251/129.03 |
| 2014/0249412 | A1 | 9/2014 | Yamamoto | |
| 2018/0126147 | A1 * | 5/2018 | Hakim | A61B 5/032 |
| 2019/0085982 | A1 * | 3/2019 | Ting | F16K 1/14 |
| 2019/0353272 | A1 * | 11/2019 | Grandvallet | F16K 11/168 |
| 2020/0016306 | A1 * | 1/2020 | Weber | A61M 1/064 |
| 2021/0187171 | A1 * | 6/2021 | Collinson | A61M 1/75 |
| 2022/0176032 | A1 | 6/2022 | Randolph et al. | |
| 2022/0330867 | A1 * | 10/2022 | Conley | A61M 1/74 |

* cited by examiner

PORTABLE SUCTION SYSTEM

RELATED APPLICATIONS

This application claims priority to and the benefit of U.S. Provisional Patent Application No. 63/417,406 filed on Oct. 19, 2022, which is incorporated herein by reference in its entirety for all purposes.

BACKGROUND

Many military and civilian patients require treatment provided by medical systems in the field but cannot receive such treatment because such systems remain only deployed in medical treatment facilities due to size, power requirements, climate constraints, and other factors. For example, the standard of care for patients requiring in a medical or trauma facility is 0-550 mmHg suction pressure from a wall-mounted or battery powered unit, and is capable of using a variety of suction attachments (e.g., suction hoses of varying lengths, catheters including a variety of soft and hard catheters), each for a different purpose.

Currently, many first responders and military medical personnel improvise suction treatment at the point of injury, using low suction, manual devices as stop-gap measures (e.g., bulb suction, syringe suction, airway positioning procedures, etc.) until the patient reaches either an equipped transportation vehicle or an emergency care facility. Conventional suction devices are large, require significant power, have limited duration of effectiveness, and are problematic in adverse conditions. As such, conventional suction solutions compromise the patient's ability to survive.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides a device comprising: a motor assembly and a barrel drive rotatably driven by the motor assembly about a barrel axis. A cam is formed in the barrel drive. The device further includes a first follower positioned within the cam; a second follower positioned within the cam; a first rod coupled to the first follower; a second rod coupled to the second follower; a pressure regulator including a cavity; a valve in fluid communication with the cavity; and a pressure sensor in fluid communication with the cavity.

In some embodiments, operation of the motor assembly is adjusted in response to detecting a pressure in the cavity with the pressure sensor.

In some embodiments, operation of the valve is adjusted in response to detecting a pressure in the cavity with the pressure sensor.

In some embodiments, the device further includes a processor electrically coupled to the motor assembly, the pressure sensor, and the valve.

In some embodiments, the motor assembly includes an electric motor, a gear set, a transmission, a first position sensor, and a second position sensor.

In some embodiments, the barrel drive includes an outer cylindrical surface, and the cam is formed in the outer cylindrical surface of the barrel drive.

In some embodiments, the cam extends 360 degrees around the outer cylindrical surface.

In some embodiments, the first rod defines a first rod axis, and the second rod defines a second rod axis, and wherein the first rod axis is parallel to the second rod axis.

In some embodiments, the first rod axis is parallel to the barrel axis.

In some embodiments, the device further includes a first seal and a second seal, wherein the first rod extends through the first seal and is movable with respect to the first seal, and the second rod extends through the second seal and is movable with respect to the second seal.

In some embodiments, the first rod includes a flange formed at an end of the first rod, and wherein the first rod includes a groove that at least partially defines the flange.

In some embodiments, the regulator includes an air inlet, a first port, and a second port, wherein the first port is in fluid communication with the cavity, and the second port is in fluid communication with the pressure sensor.

In some embodiments, the regulator includes a passageway including a metered insert.

In some embodiments, the passageway extends between the air inlet and the pressure sensor.

In some embodiments, the device further includes a housing that at least partially defines a recess, and wherein a sensor configured to detect the presence of an attachment is positioned within the recess.

In some embodiments, the device further includes a status display and a user interface, wherein a pressure in the cavity is adjustable in response to receiving a user input at the user interface.

In some embodiments, the device is placed in a parked configuration in response to deenergizing the device, wherein the parked configuration includes the first rod and the second rod at the same position along the barrel axis.

In some embodiments, the device includes a battery assembly, and wherein the battery assembly is removable.

In some embodiments, the device includes a latch with a plurality of teeth, a spring biasing the latch into a closed position, and wherein the housing includes a cover with a plurality of teeth engaged with the plurality of teeth on the latch, and wherein the cover is moveable in response to the latch moved against the spring bias into an open position.

One aspect of the present disclosure provides a device comprising: a bag; a vacuum connector; a first stem coupled to the vacuum connector; wherein the first stem includes a first cylinder and a first cavity; and a second stem coupled to the vacuum connector; wherein the second stem includes a second cylinder and a second cavity. The device further includes a first piston positioned within the first cylinder and movable with respect to the first cylinder; a second piston position within the second cylinder and movable with respect to the second cylinder; a first bag port extending between the first cavity and the bag; and a second bag port extending between the second cavity and the bag.

In some embodiments, the bag is flexible.

In some embodiments, the first cavity is at least partially defined by the first piston; and wherein the second cavity is at least partially defined by the second piston.

In some embodiments, the device further includes a first one-way valve positioned between the first stem and the vacuum connector, and a second one-way valve positioned between the second stem and the vacuum connector.

In some embodiments, the first bag port extends along a first port axis and the first cylinder extends along a first cylinder axis, and wherein the first port axis is orthogonal to the first cylinder axis.

In some embodiments, the second bag port extends along a second port axis and the second cylinder extends along a second cylinder axis, and wherein the second port axis is orthogonal to the second cylinder axis.

In some embodiments, the second cylinder axis is parallel to the first cylinder axis.

In some embodiments, the first piston includes a first notch and the second piston includes a second notch.

In some embodiments, the device includes a cap assembly coupled to the bag, wherein the cap assembly is movable between a vent position, a closed position, and a removed position.

In some embodiments, the device includes a cover and an actuator that extends from the cover, wherein the actuator deflects in response to activation by a user.

In some embodiments, the device includes a regulator stem assembly coupled to the vacuum connector, wherein the regulator stem assembly includes a first aperture, a second aperture, a first one-way valve, and a second one-way valve.

One aspect of the present disclosure provides a system comprising a first device and a second device. The first device includes a housing defining a recess; a motor assembly positioned within the housing; a first rod at least partially extending from the housing into the recess; and a second rod at least partially extending from the housing into the recess. The first rod and the second rod are driven in response to energization of the motor assembly. The second device is at least partially positioned within the recess. The second device includes: a bag; a vacuum connector; a first piston coupled to the first rod; and a second piston coupled to the second rod. The second device is removable from the first device.

In some embodiments, the second device includes a cover and an actuator extending from the cover, wherein the second device is released from the first device in response to actuation of the actuator.

In some embodiments, the first device includes a pressure regulator including a cavity; a valve in fluid communication with the cavity; and a pressure sensor in fluid communication with the cavity.

In some embodiments, the second device includes a regulator stem assembly in fluid communication with the pressure regulator.

In some embodiments, the first rod is driven out of phase with the second rod.

Other aspects of the disclosure will become apparent by consideration of the detailed description and accompanying drawings.

BRIEF DESCRIPTION OF THE DRAWINGS

The accompanying figures and examples are provided by way of illustration and not by way of limitation. The foregoing aspects and other features of the disclosure are explained in the following description, taken in connection with the accompanying example figures (also "FIG.") relating to one or more embodiments.

Figure 1:
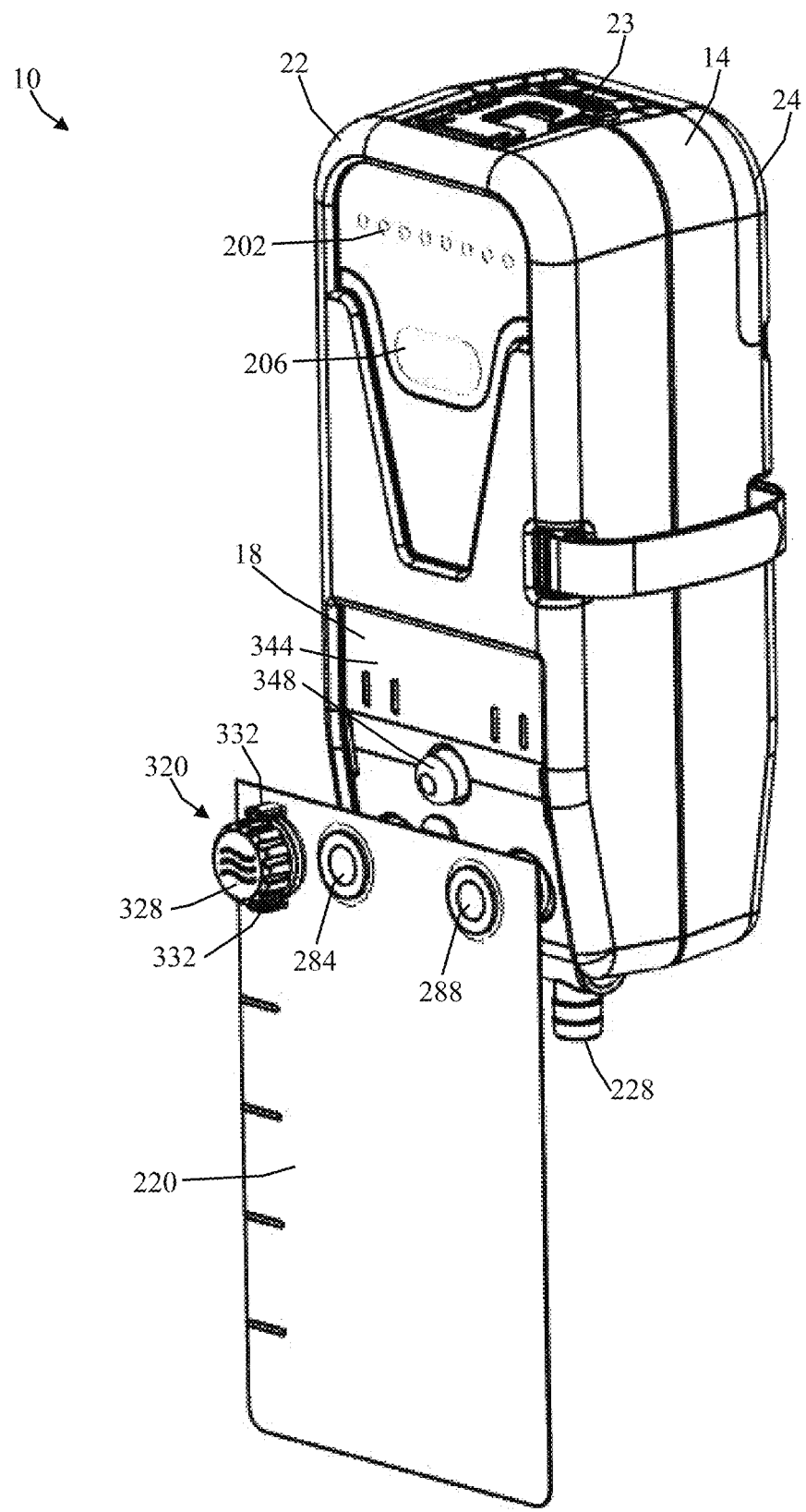
FIG. 1 is a perspective view of a portable suction system including a pump device and a bag device.

Before any embodiments are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

"About" and "approximately" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations when interpreted in the alternative ("or").

Moreover, the present disclosure also contemplates that in some embodiments, any feature or combination of features set forth herein can be excluded or omitted. To illustrate, if the specification states that an apparatus comprises components A, B, and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the terms "processor", "central processing unit", or "CPU" are used interchangeably and refer to a device that is able to read a program from a computer memory (e.g., ROM or other computer memory) and perform a set of steps according to the program. As used herein, the term "processor" (e.g., a microprocessor, a microcontroller, a processing unit, or other suitable programmable device) can include, among other things, a control unit, an arithmetic logic unit ("ALC"), and a plurality of registers and can be implemented using a known computer architecture (e.g., a modified Harvard architecture, a von Neumann architecture, etc.). In some embodiments, the processor is a microprocessor that can be configured to communicate in a stand-alone and/or a distributed environment and can be configured to communicate via wired or wireless communications with other processors, where such one or more processor can be configured to operate on one or more processor-controlled devices that can be similar or different devices.

As used herein, the term "memory" is any memory storage and is a non-transitory computer readable medium. The memory can include, for example, a program storage area and the data storage area. The program storage area and the data storage area can include combinations of different types of memory, such as a ROM, a RAM (e.g., DRAM, SDRAM, etc.), EEPROM, flash memory, a hard disk, a SD card, or other suitable magnetic, optical, physical, or electronic memory devices. The processor can be connected to the memory and execute software instructions that are capable of being stored in a RAM of the memory (e.g., during execution), a ROM of the memory (e.g., on a generally permanent bases), or another non-transitory computer readable medium such as another memory or a disc. In some embodiments, the memory includes one or more processor-readable and accessible memory elements and/or components that can be internal to the processor-controlled device, external to the processor-controlled device, and can be accessed via a wired or wireless network. Software included in the implementation of the methods disclosed herein can be stored in the memory. The software includes, for example, firmware, one or more applications, program data, filters, rules, one or more program modules, and other executable instructions. For example, the processor can be configured to retrieve from the memory and execute, among other things, instructions related to the processes and methods described herein.

As used herein, the term "computer readable medium" refers to any device or system for storing and providing information (e.g., data and instructions) to a computer processor. Examples of computer readable media include, but are not limited to, DVDs, CDs, hard disk drives, magnetic tape, and servers for streaming media over networks, whether local or distant (e.g., cloud-based).

The term "coupled," as used herein, is defined as "connected," although not necessarily directly, and not necessarily mechanically. The term coupled is to be understood to mean physically, magnetically, chemically, fluidly, electrically, or otherwise coupled, connected, or linked and does not exclude the presence of intermediate elements between the coupled elements absent specific contrary language.

As used herein, the term "in electronic communication" refers to electrical devices (e.g., computers, processors, etc.) that are configured to communicate with one another through direct or indirect signaling. Likewise, a computer configured to transmit (e.g., through cables, wires, infrared signals, telephone lines, airwaves, etc.) information to another computer or device, is in electronic communication with the other computer or device.

As used herein, the term "vacuum" or "suction" refers to a gaseous pressure less than atmospheric pressure.

Unless otherwise defined, all technical terms used herein have the same meaning as commonly understood by one of ordinary skill in the art to which this disclosure belongs.

With reference to FIG. 1, a portable suction system 10 includes a pump device 14 and a bag device 18. The portable suction system 10 described herein provides a safe and effective solution for use in the field (e.g., during transportation to a transportation vehicle, in the vehicle to a medical facility, or in a situation where moving a patient is impractical or impossible for an extended period of time).

Figure 2:
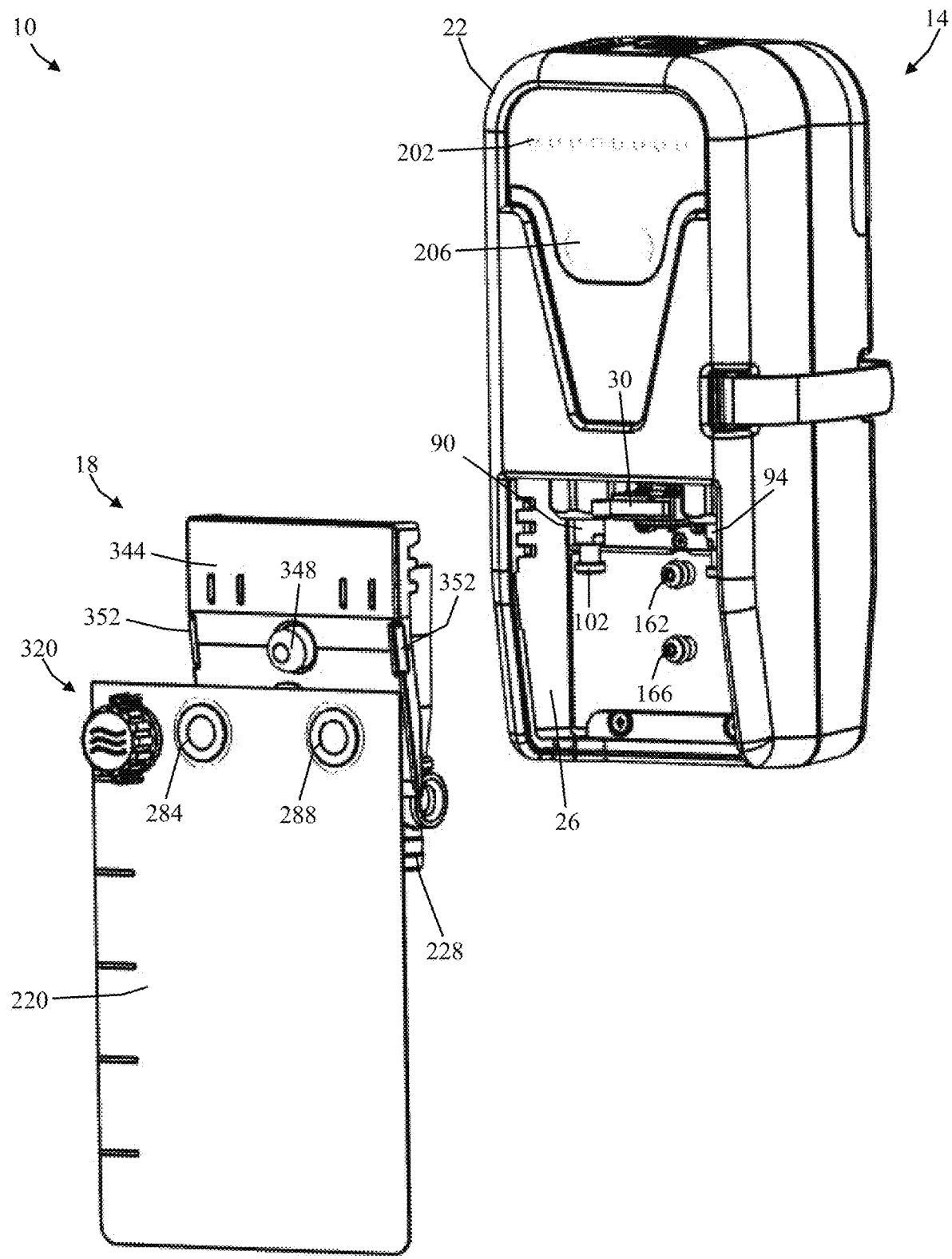
FIG. 2 is a perspective view of the portable suction system of FIG. 1, with the bag device shown removed from the pump device.

With reference to FIG. 2, the bag device 18 is removable from the pump device 14. In some embodiments, the bag device 18 is a single-use disposable. The pump device 14 includes a housing 22 that defines a recess 26. In the illustrated embodiment, the bag device 18 is at least partially positioned within the recess 26 when the bag device 18 is coupled to the pump device 14. In the illustrated embodiment, the pump device 14 includes a sensor 30 positioned within the recess 26, and the sensor 30 is configured to detect the presence of the bag device 18 when the bag device 18 is positioned within the recess 26.

Figure 5:
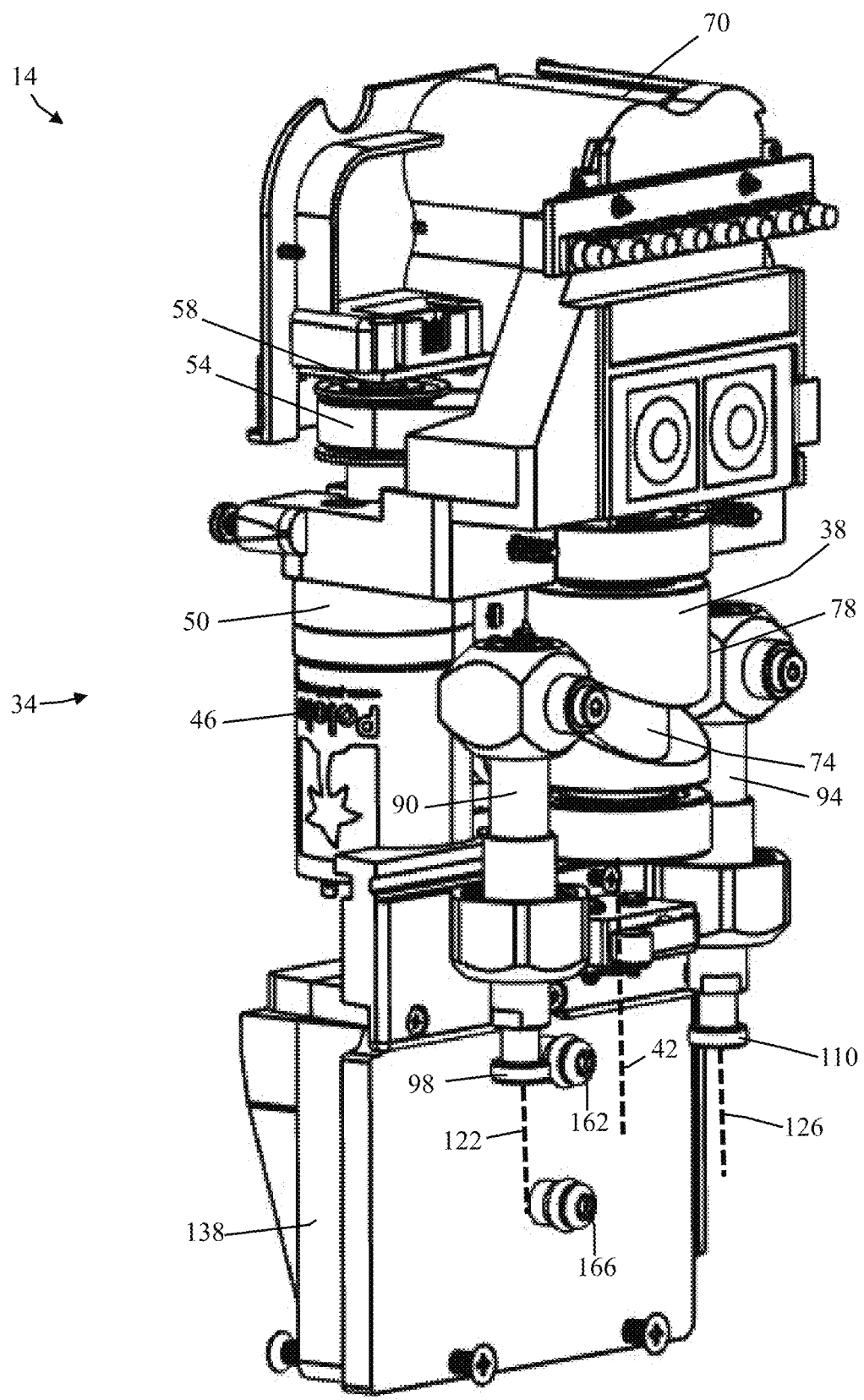
FIG. 5 is a perspective view of the pump device of FIG. 1, shown with a housing removed.
Figure 6:
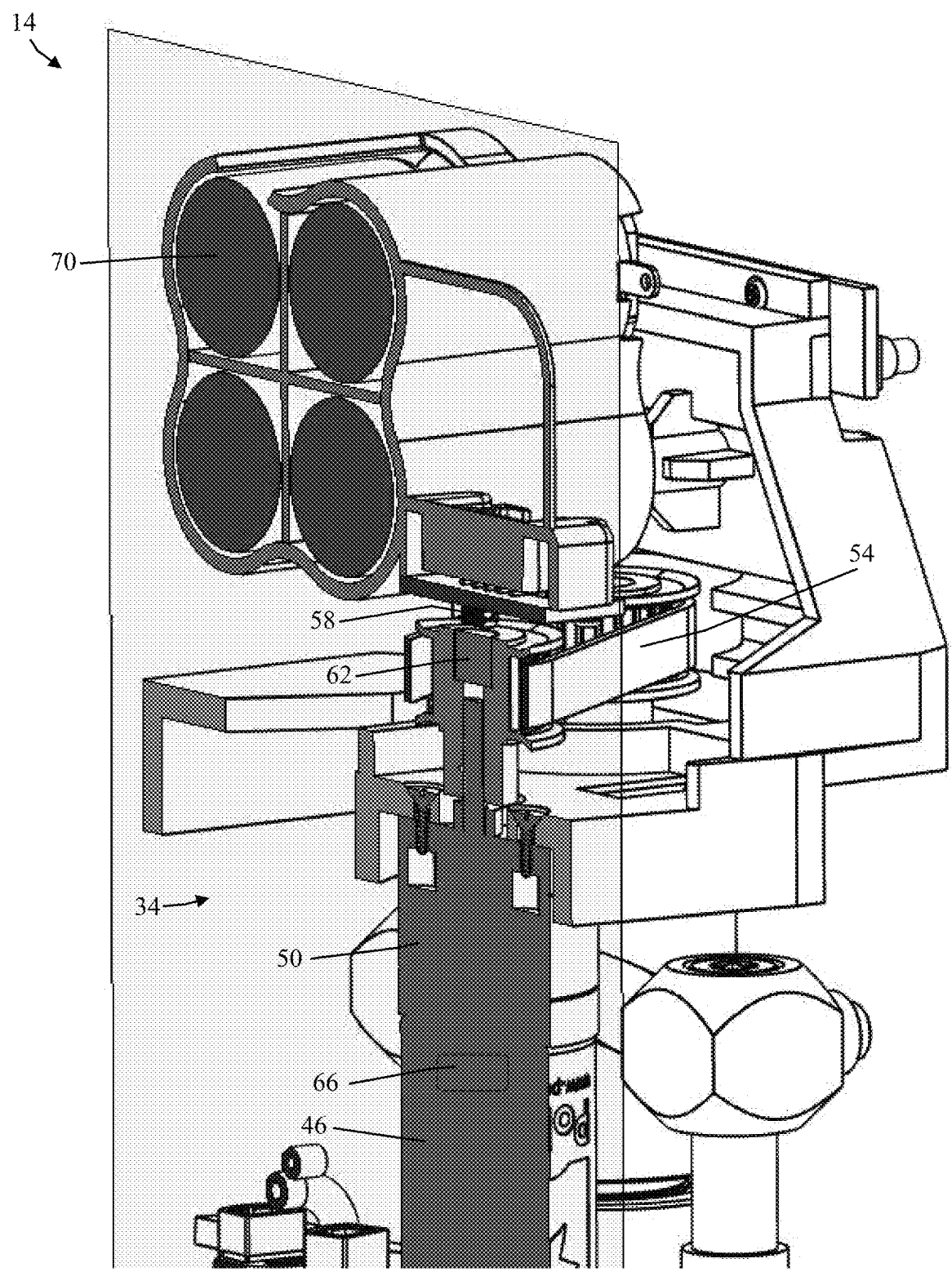
FIG. 6 is a perspective cross-sectional view of the pump device of FIG. 1.
Figure 7:
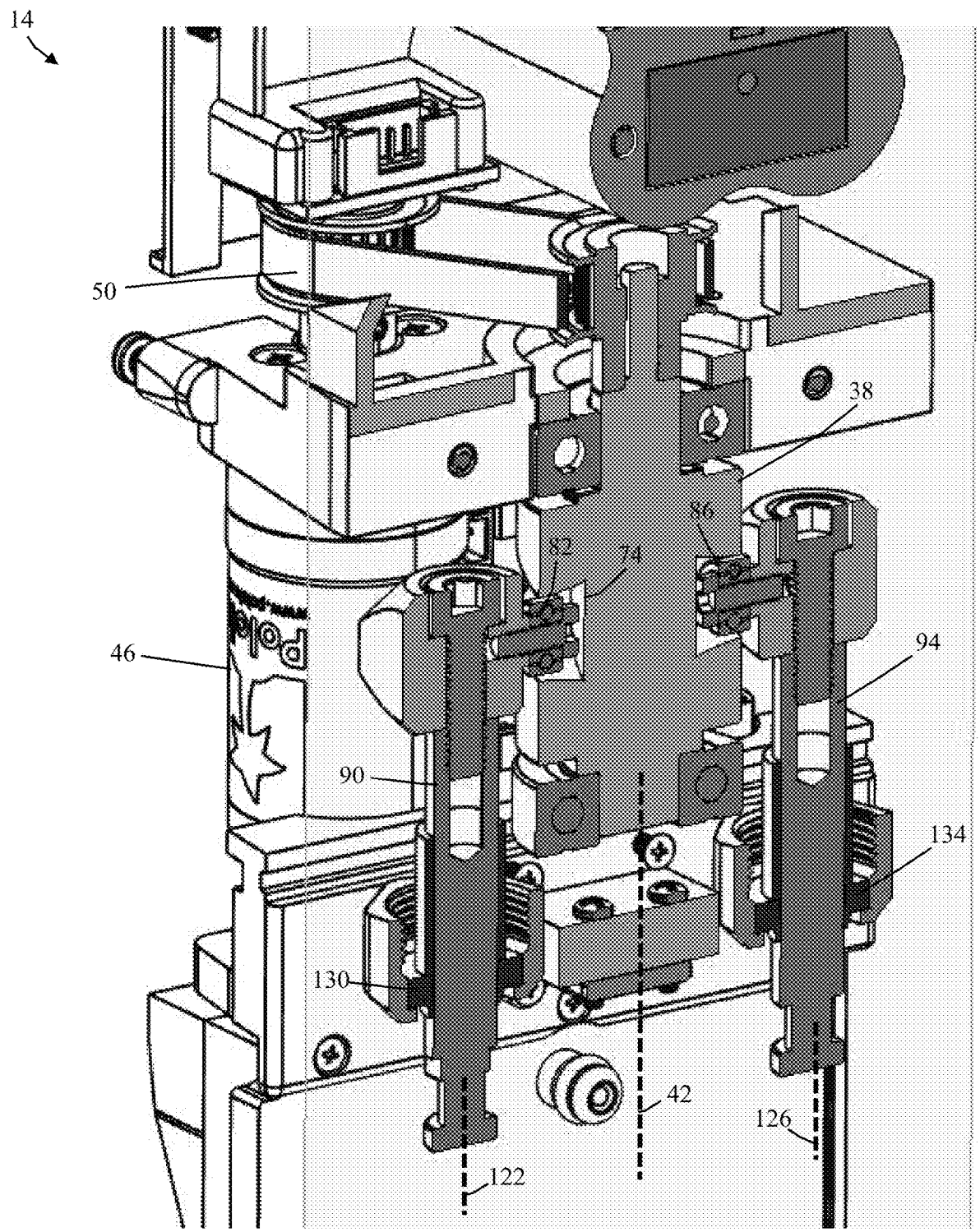
FIG. 7 is a perspective cross-sectional view of the pump device of FIG. 1.

With reference to FIGS. 5, 6, and 7, the pump device 14 includes a motor assembly 34 coupled to a barrel drive 38. In the illustrated embodiment, the motor assembly 34 and the barrel drive 38 are positioned within the housing 22. In the illustrated embodiment, the barrel drive 38 is rotatably driven by the motor assembly 34 about a barrel axis 42. The motor assembly 34 includes an electric motor 46, a gear set 50, and a transmission 54. In some embodiments, the electric motor 46 is a DC motor, a brushless DC motor, a reluctance motor, an induction motor, a permanent magnet motor, or other suitable motor. In some embodiments, the gear set 50 is a planetary gear set. In some embodiments, the transmission 54 is a belt transmission.

With reference to FIG. 6, the motor assembly 34 includes a first position sensor 58 (e.g., a Giant Magnetoresistance "GMR" sensor). The first position sensor 58 detects a magnetic field resulting from the position of a magnet 62. In some embodiments, the motor assembly 34 also includes a second position sensor 66 (e.g., a Hall-effect sensor). The second position sensor 66 may advantageously provide increased position resolution detection of the position of the electric motor 46. In the illustrated embodiment, the absolute position of the electric motor 46 and correspondingly the rods 90, 94 are detectable with the first position sensor 58 and the second position sensor 66.

With reference to FIG. 6, the pump device 14 includes a battery assembly 70. In some embodiments, the battery assembly 70 is removable and replaceable with another battery assembly. In some embodiments, the battery assembly 70 includes CR 123 batteries. In some embodiments, the battery assembly 70 includes Lithium-ion batteries.

Figure 20:
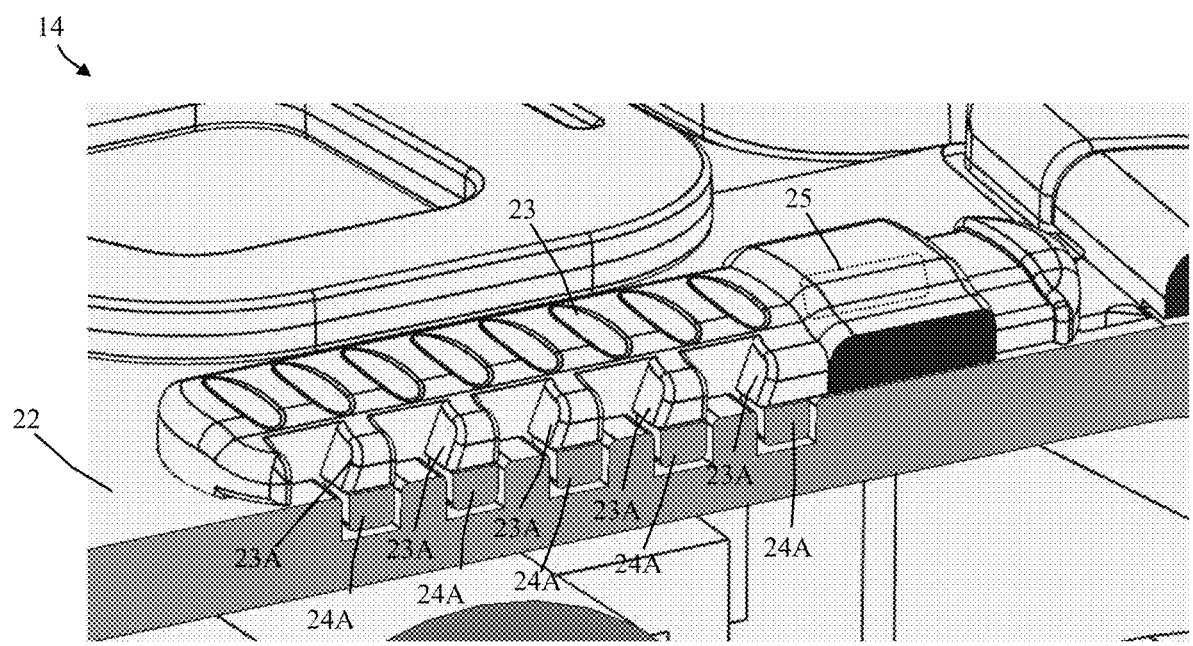
FIG. 20 is a perspective view of a latch in a closed position with teeth interfacing with teeth formed on a cover.
Figure 21:
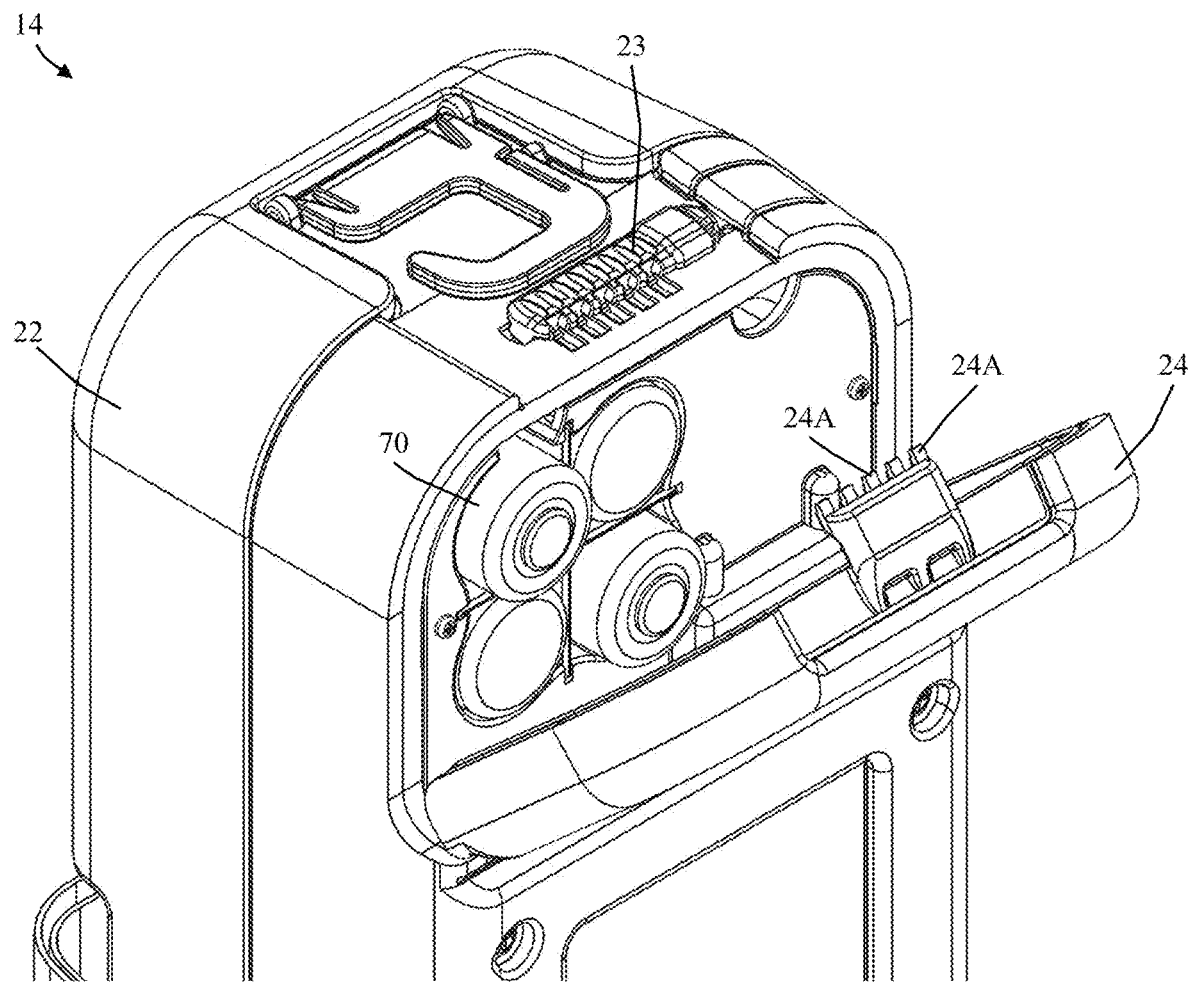
FIG. 21 is a perspective view of a cover and latch in an open position.

With reference to FIGS. 20 and 21, the pump device 14 includes a latch 23 to secure a movable cover 24. In the illustrated embodiment, the cover 24 is openable to gain access to the battery assembly 70. The latch 23 includes a plurality of teeth 23A, and a spring 25 biases the latch 23 into a closed position (FIG. 20). The cover 24 includes a plurality of teeth 24A that correspond with and overlap the plurality of teeth 23A on the latch 23A in the closed position. The cover 24 is moveable to an open position (FIG. 21) in response to the latch 23 being moved against the spring 25 bias, which separates the teeth 23A from the teeth 24A. The teeth 23A, 24A increase the captured area in sheer contact without increasing the latch size or required movement. In the illustrated embodiment, the latch 23 moves to the open position by moving the distance of one tooth.

Figure 8:
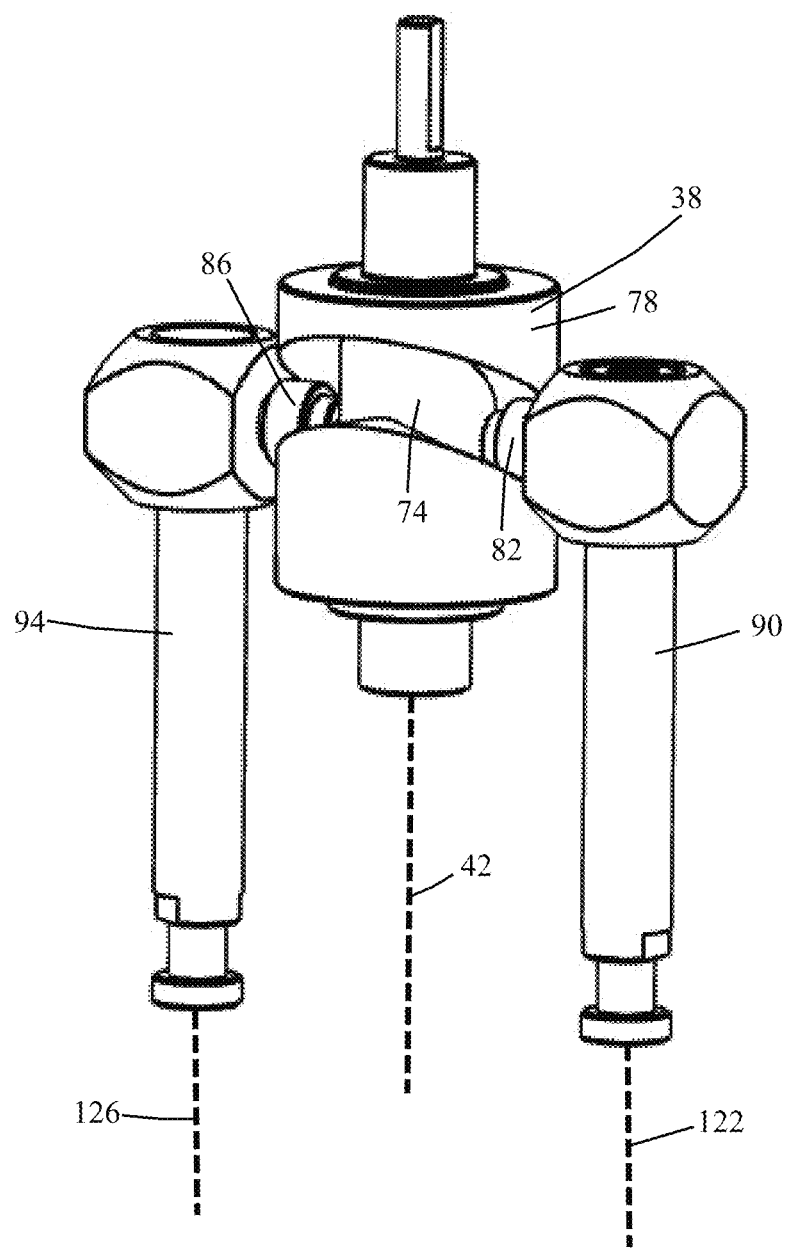
FIG. 8 is a perspective view of a barrel drive, a first rod, and a second rod.

With reference to FIGS. 7 and 8, a cam 74 is formed in the barrel drive 38. In the illustrated embodiment, the barrel drive 38 includes an outer cylindrical surface 78, and the cam 74 is formed in the outer cylindrical surface 78 of the barrel drive 38. In the illustrated embodiment, the cam 74 extends 360 degrees around the outer cylindrical surface 78. A first follower 82 is positioned within the cam 74, and a second follower 86 is positioned within the cam 74. In other words, more than one follower 82, 86 is positioned within the cam 74. The followers 82, 86 slide within the cam 74 as the barrel drive 38 rotates about the barrel axis 42.

Figure 3:
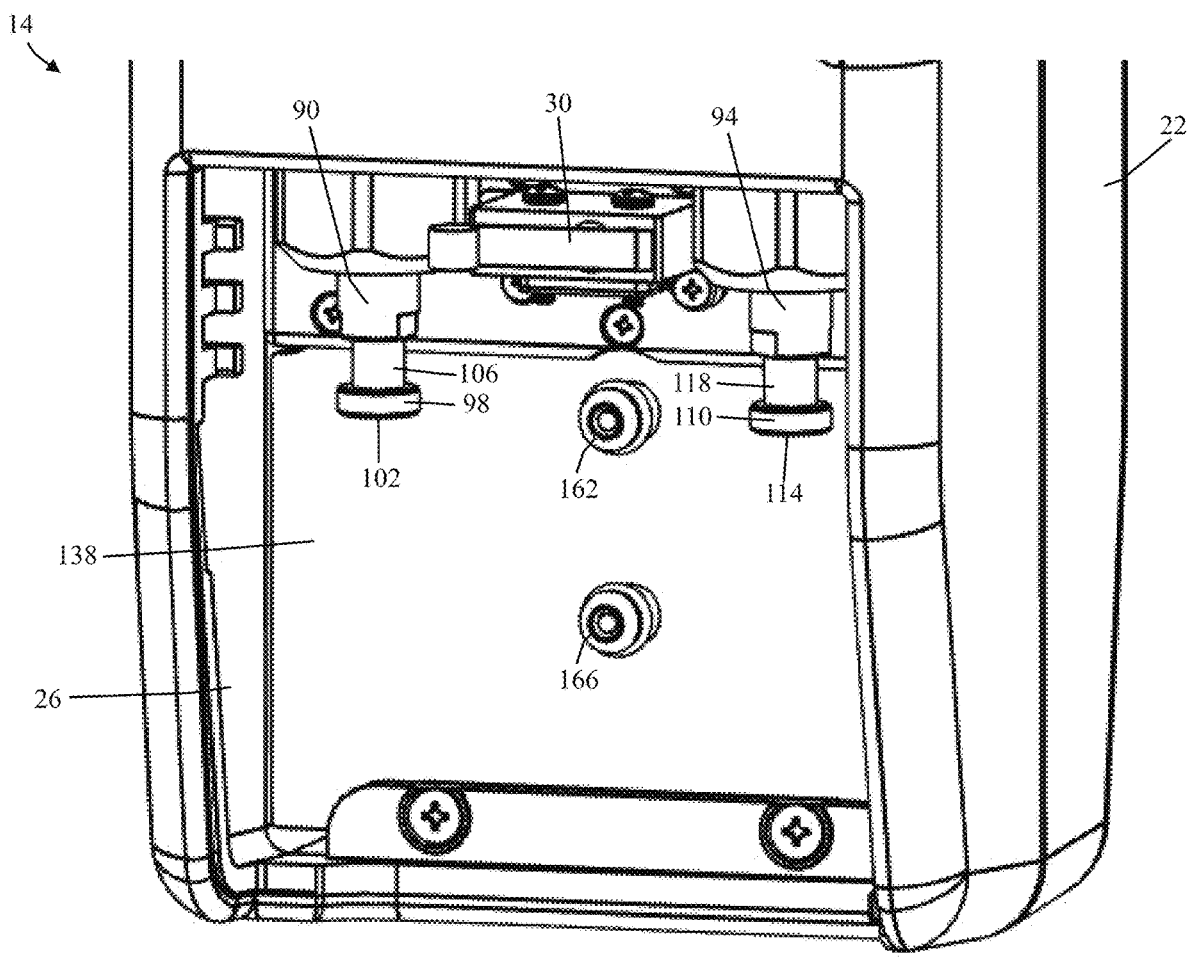
FIG. 3 is a partial perspective view of the pump device of FIG. 1.

With continued reference to FIG. 7, the pump device 14 includes a first rod 90 coupled to the first follower 82 and a second rod 94 coupled to the second follower 86. In the illustrated embodiment, the pump device 14 includes two rods 90, 94 driven in response to energization of the motor assembly 34. In other embodiments, the pump device 14 includes any number of rods driven by the motor assembly. The first rod 90 at least partially extends from the housing 22 into the recess 26, and the second rod 94 at least partially extends from the housing 22 into the recess 26 (FIG. 3). In the illustrated embodiment, the rods 90, 94 are driven in an alternating fashion such that, for example, the first rod 90 is extending from the housing 22 as the second rod 94 is retracting into the housing 22. In other words, the first rod 90 is driven out of phase with the second rod 94.

The first rod 90 includes a flange 98 formed at an end 102 of the first rod 90. In the illustrated embodiment, the first rod 90 includes a groove 106 that at least partially defines the flange 98. Similarly, the second rod 94 includes a flange 110 and a groove 118 formed at an end 114 of the second rod 94. As detailed further herein, the ends 102, 114 of the rods 90, 94 are removably coupled to the bag portion 18. The first rod 90 defines a first rod axis 122 and the second rod 94 defines a second rod axis 126. In the illustrated embodiment, the first rod axis 122 is parallel to the second rod axis 126. In the illustrated embodiment, the first rod axis 122 and the second rod axis 126 are parallel to the barrel axis 42.

With continued reference to FIG. 7, the pump device 14 further includes a first seal 130 and a second seal 134. The first rod 90 extends through the first seal 130 and is movable with respect to the first seal 90. The second rod 94 extends through the second seal 134 and is movable with respect to the second seal 134. As such, the pump device 14 remains sealed to the external environment that the system 10 is used in.

Figure 9:
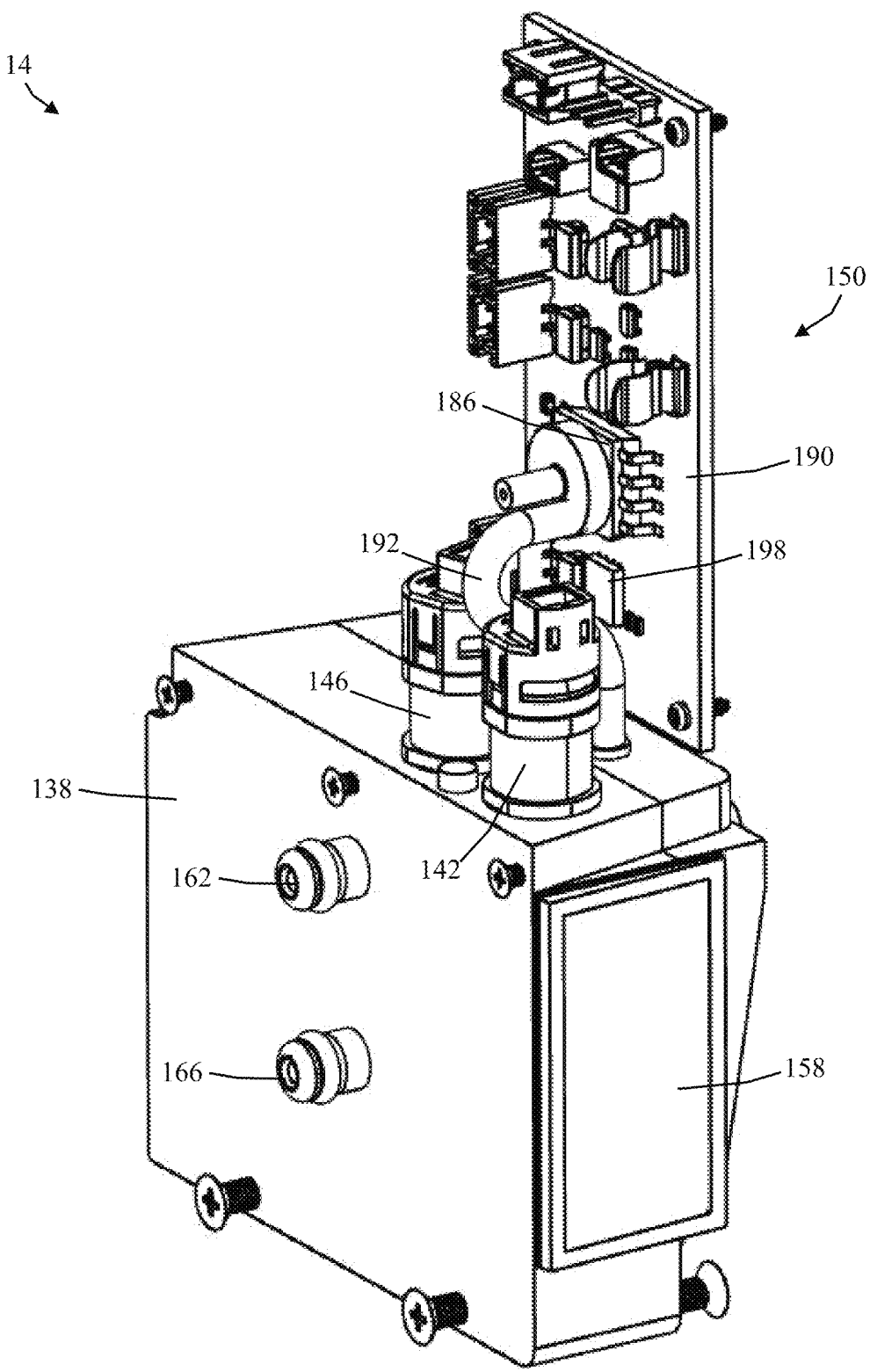
FIG. 9 is a perspective view of a pressure regulator and a circuit board assembly.
Figure 10:
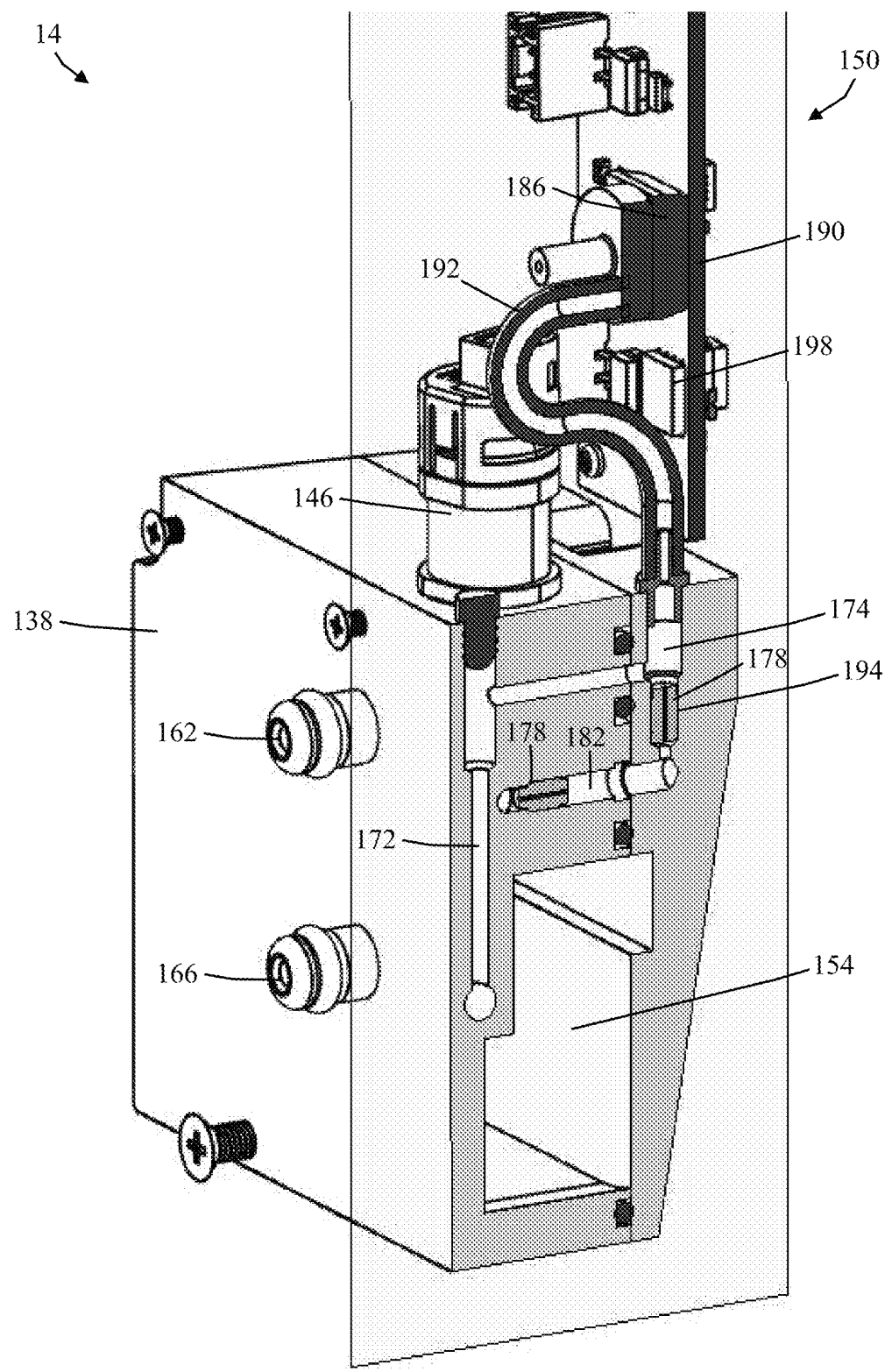
FIG. 10 is a perspective cross-sectional view of the pressure regulator and circuit board assembly of FIG. 9.
Figure 11:
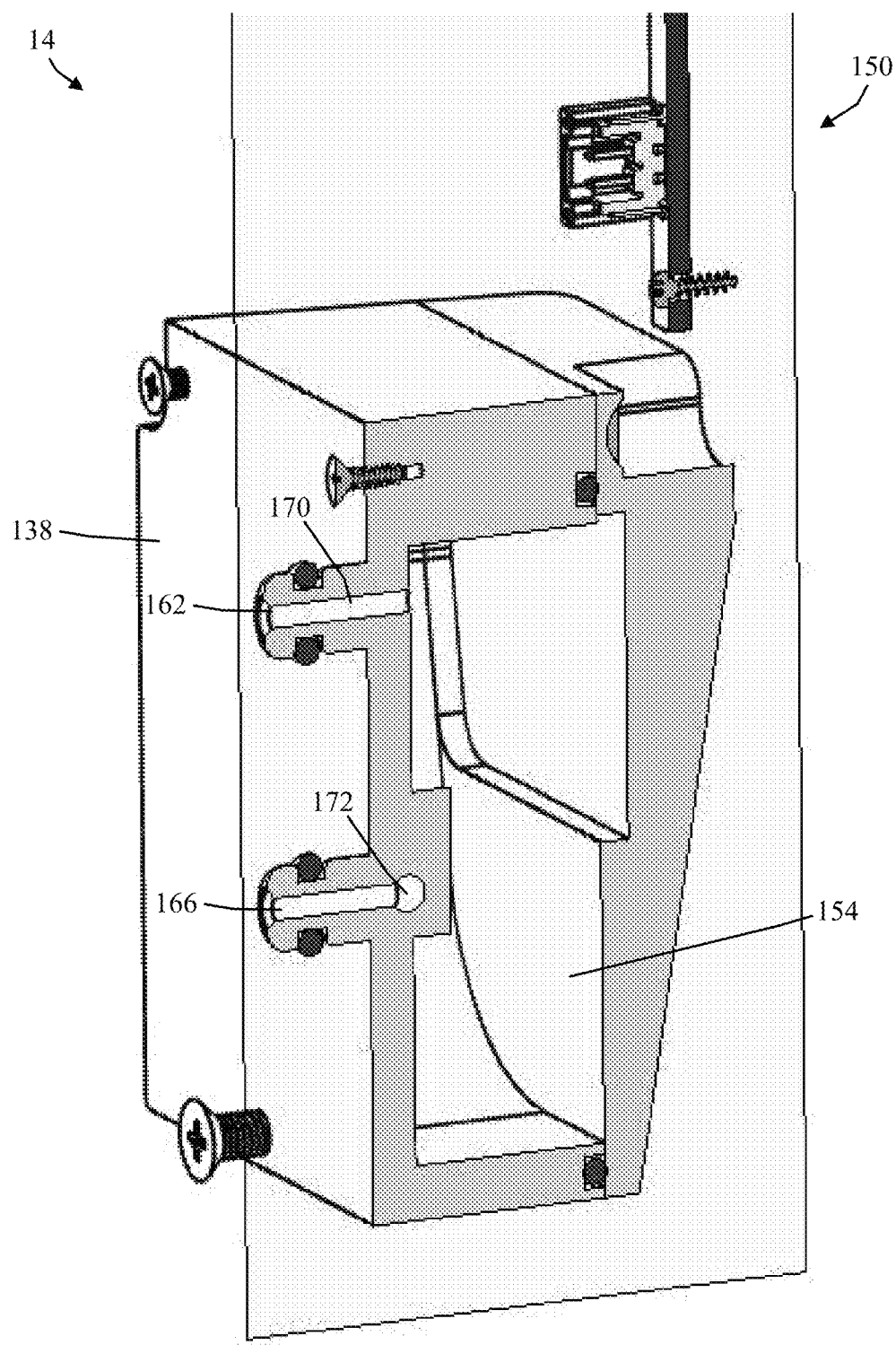
FIG. 11 is a partial perspective cross-sectional view of the pressure regulator of FIG. 9.

With reference to FIG. 9, the pump device 14 further includes a pressure regulator 138, a first valve 142, a second valve 146, and a circuit board assembly 150. The pressure regulator 138 defines a cavity 154. The pressure regulator 138 includes an air inlet 158, a first port 162, and a second port 166. In the illustrated embodiment, the first port 162 is in fluid communication with the cavity 154 by a passageway 170. In the illustrated embodiment, the second port 166 is in fluid communication with a sensing chamber 174 by a passageway 172. In some embodiments, the pressure regulator 138 includes one or more metering inserts 178 that are positioned with passageways to limit the flow of air, thereby creating metered air flow. The metered pneumatic air bleed system advantageously allows for the regulation and pressure measurement of the suction side of the pump. The regulator 138 allows for pressure recovery in measurement after the pump goes through a low pressure event (e.g., a high suction pressure).

Figure 12:
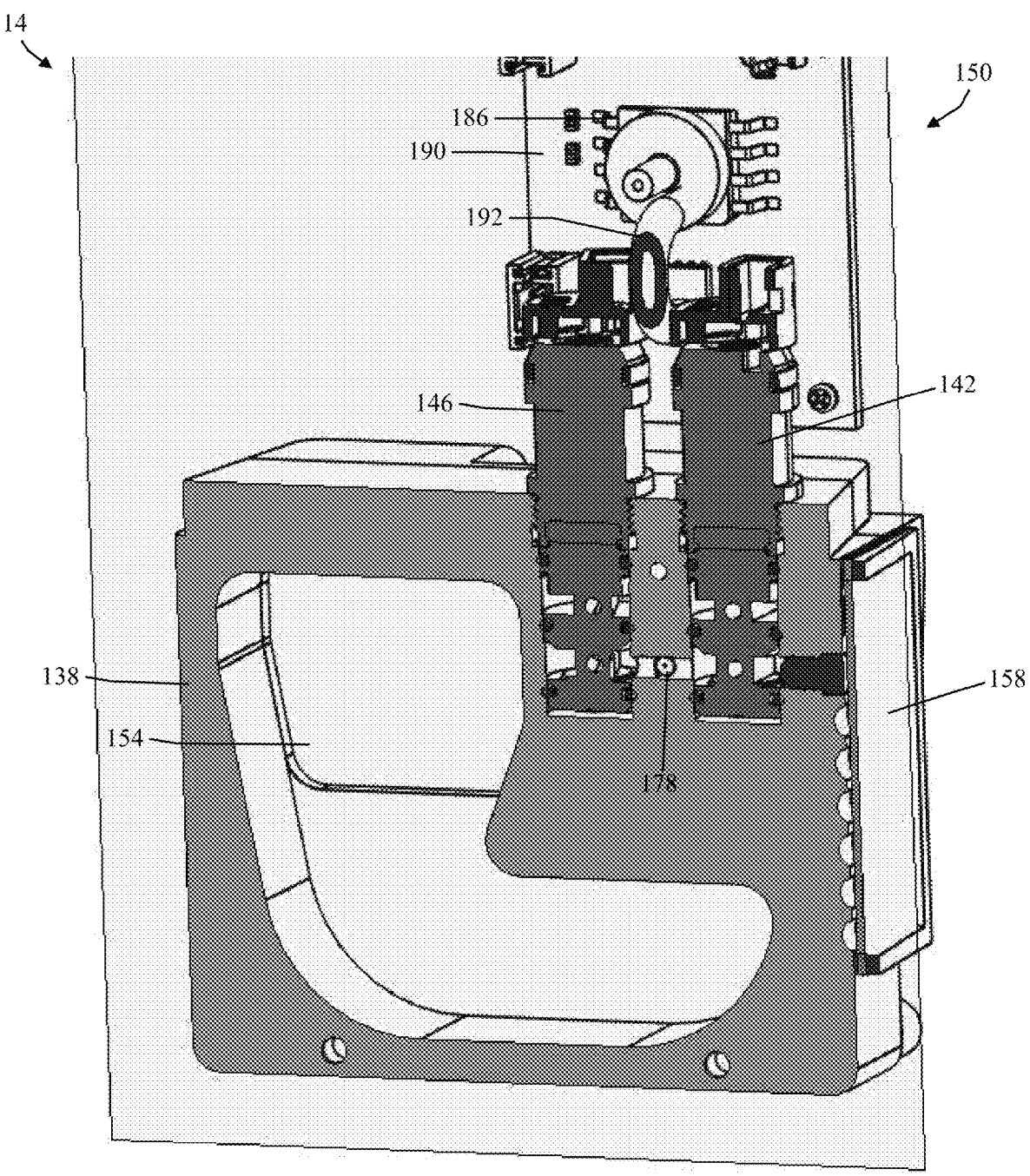
FIG. 12 is a partial perspective cross-sectional view of the pressure regulator and circuit board assembly of FIG. 9.

With reference to FIG. 12, the valves 142, 146 control the flow of ambient air into the cavity 154. In some embodiments, the valves 142, 146a are electronically controlled by the circuit board assembly 150 to adjust the pressure within the cavity 154. In the illustrated embodiment, the first valve 142 and the second valve 146 are "bullet valves" and are electronically controlled to move between an open position and a closed position. In the illustrated embodiment, the two pneumatic valves 142, 146 are positioned in series with each other. A passageway 182 from the air inlet 158 includes a metered insert 178 and connects between the two pneumatic valves 142, 146 to provide pressure control with high accuracy over a broad range of pressure and flow conditions. In some embodiments, the first valve 142 is controlled for large adjustments of pressure and the second valve 146 is controlled for small adjustments of pressure. In some embodiments, only one valve is utilized. In some embodiments, any number of valves are utilized to regulate the pressure within the cavity.

With continued reference to FIG. 9, the circuit board assembly 150 includes a pressure sensor 186 mounted on a circuit board 190. The pressure sensor 186 is in fluid communication with the cavity 154 in the pressure regulator 138. Specifically, in the illustrated embodiment, the pressure sensor 186 is fluidly coupled to the sensing chamber 174. In the illustrated embodiment, a flexible conduit 192 fluidly connects the pressure sensor 186 to the pressure regulator 138. In some embodiments, the cavity 154 and the sensing chamber 174 advantageously dampen the noise generated by the reciprocating rods 90, 94 to improve the measurement of pressure by the pressure sensor 186. In the illustrated embodiment, the regulator 138 includes a passageway 194 from the air inlet 158 to the sensing chamber 174 and includes a metered insert 178 positioned therein.

In some embodiments, the circuit board assembly 150 includes a processor 198 electrically coupled to the motor assembly 34, the pressure sensor 186, the valves 142, 146, or any combination thereof. In some embodiments, operation of the motor assembly 34 is adjusted in response to detecting a pressure with the pressure sensor 186. In other words, the speed or power output of the electric motor 46 is adjusted in response to pressure feedback detected by the pressure sensor 186. In some embodiments, operation of one or more valves 142, 146 is adjusted in response to detecting a pressure with the pressure sensor 186. In other words, the valves 142, 146 are adjusted in response to pressure feedback detected by the pressure sensor 186. In some embodiments, both the operation of the motor assembly 34 and the operation of the valves 142, 146 are adjusted in response to detecting a pressure with the pressure sensor 186. As such, the pump device 14 achieves precise suction pressure control by regulating the speed of the electric motor 46 and controlling valves 142, 146 based on pressure feedback from the pressure sensor 186.

In some embodiments, the pump device 14 is placed in a parked configuration in response to deenergizing (e.g., turning off) the pump device 14. With reference to FIG. 3, the parked configuration includes the first rod 90 and the second rod 94 at the same position along the barrel axis 42. In other words, the rods 90, 94 are aligned with each other. Advantageously, the parked configuration facilities removal and attachment of the bag device 18. The use of precision stopping to achieve the parked configuration aligns the rods 90, 94, and advantageously permits the bag device 18 to be quickly removed and/or replaced without adjustments or misalignments. As detailed herein, the absolute position feedback from the first sensor 58 provides feedback to accomplish the parked configuration.

With continued reference to FIG. 1, the pump device 14 includes a status display 202 and a user interface 206. In some embodiments, a pressure within the cavity 154 is adjustable in response to receiving a user input at the user interface 206. In other words, the pressure generated by the system 10 may be user selected. The system 10 is quiet to account for communication in noisy environments and has minimal illumination for low light or no light applications. The electronic interface and indicator lights are designed to reflect small unit no-light SOP implementation. In some embodiments, the system 10 can be controlled by commands entered into the pump device 14. In some embodiments, control instructions from the user may come from an external device, such as a cell phone, and be communicated by wireless communication (e.g., Bluetooth).

Figure 4:
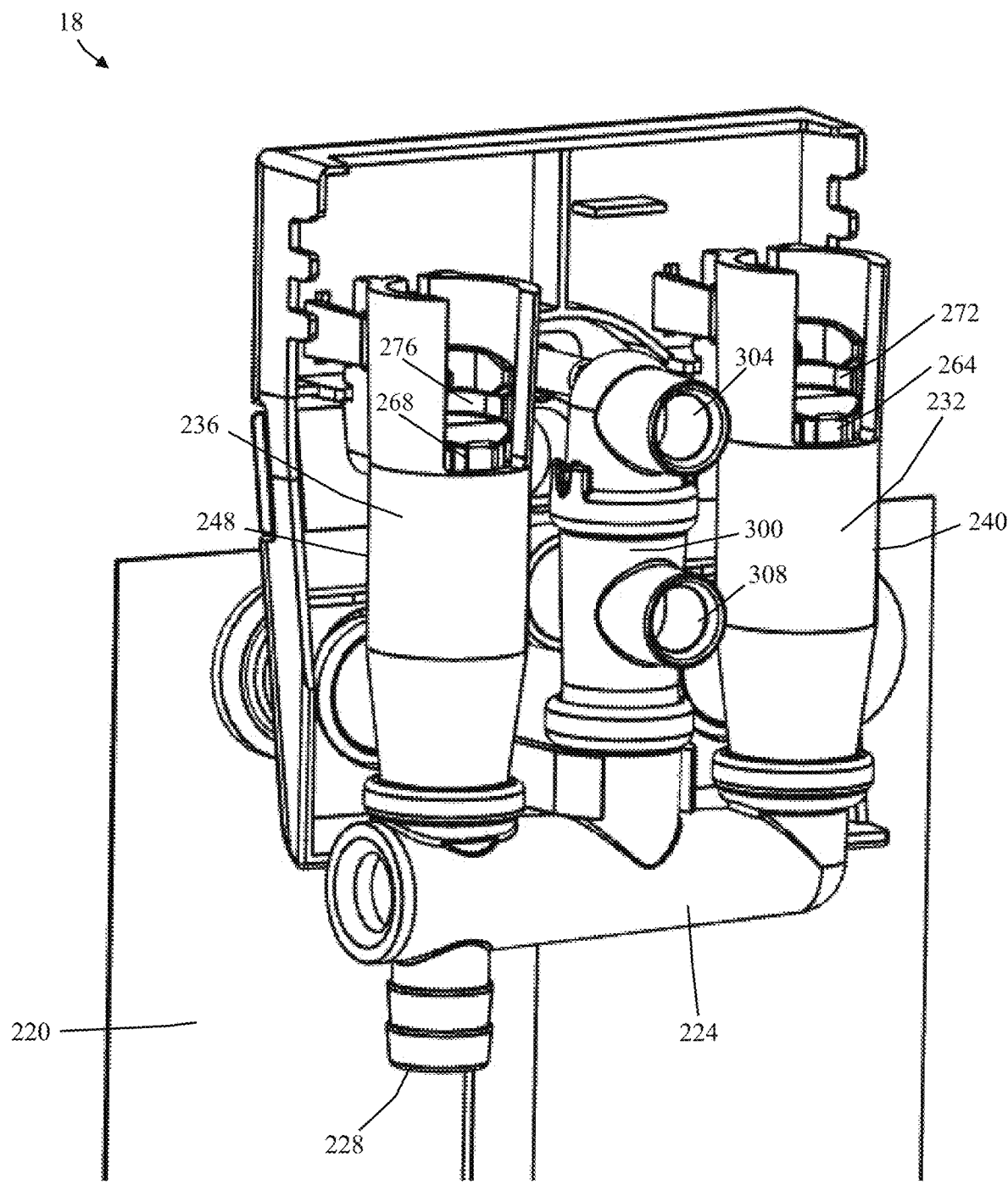
FIG. 4 is a partial perspective view of the bag device of FIG. 1.
Figure 13:
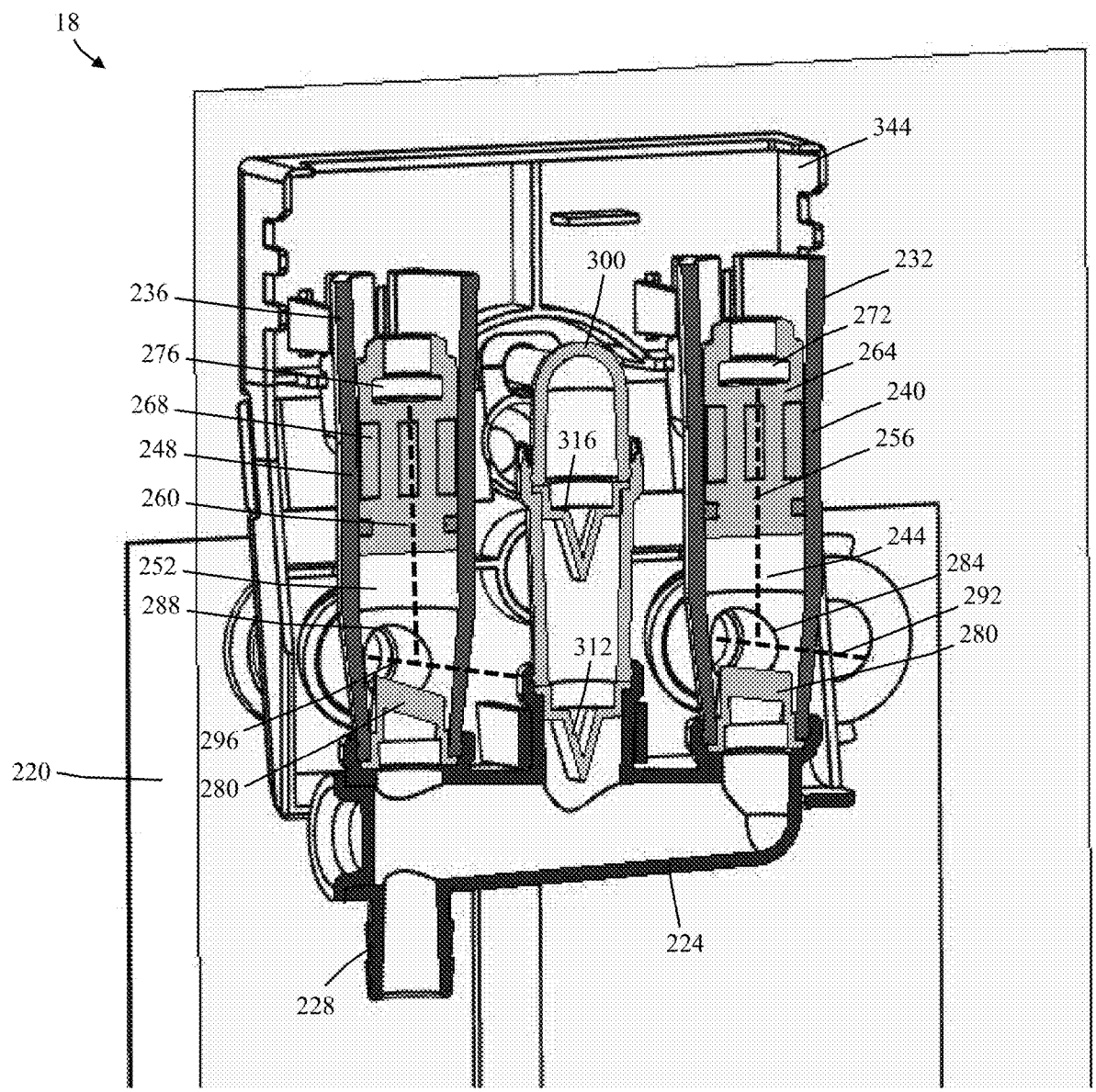
FIG. 13 is a partial perspective cross-sectional view of the bag device of FIG. 1.

With reference to FIGS. 4 and 13, the bag device 18 includes a bag 220 (e.g., a reservoir). In the illustrated embodiment, the bag 220 is flexible and is not a rigid pressure chamber. In some embodiments, the bag 220 is made of a polymer. In some embodiments, the bag 220 has a collection capacity of approximately 500 mL. The bag device 18 includes a vacuum connector 224 with a connection port 228. The connection port 228 is configured to interface with an accessory that may be utilized for different medical procedures. As detailed herein, the bag device 18 collects biohazardous waste in the field and can be easily removed and replaced from the pump device 14.

Figure 14:
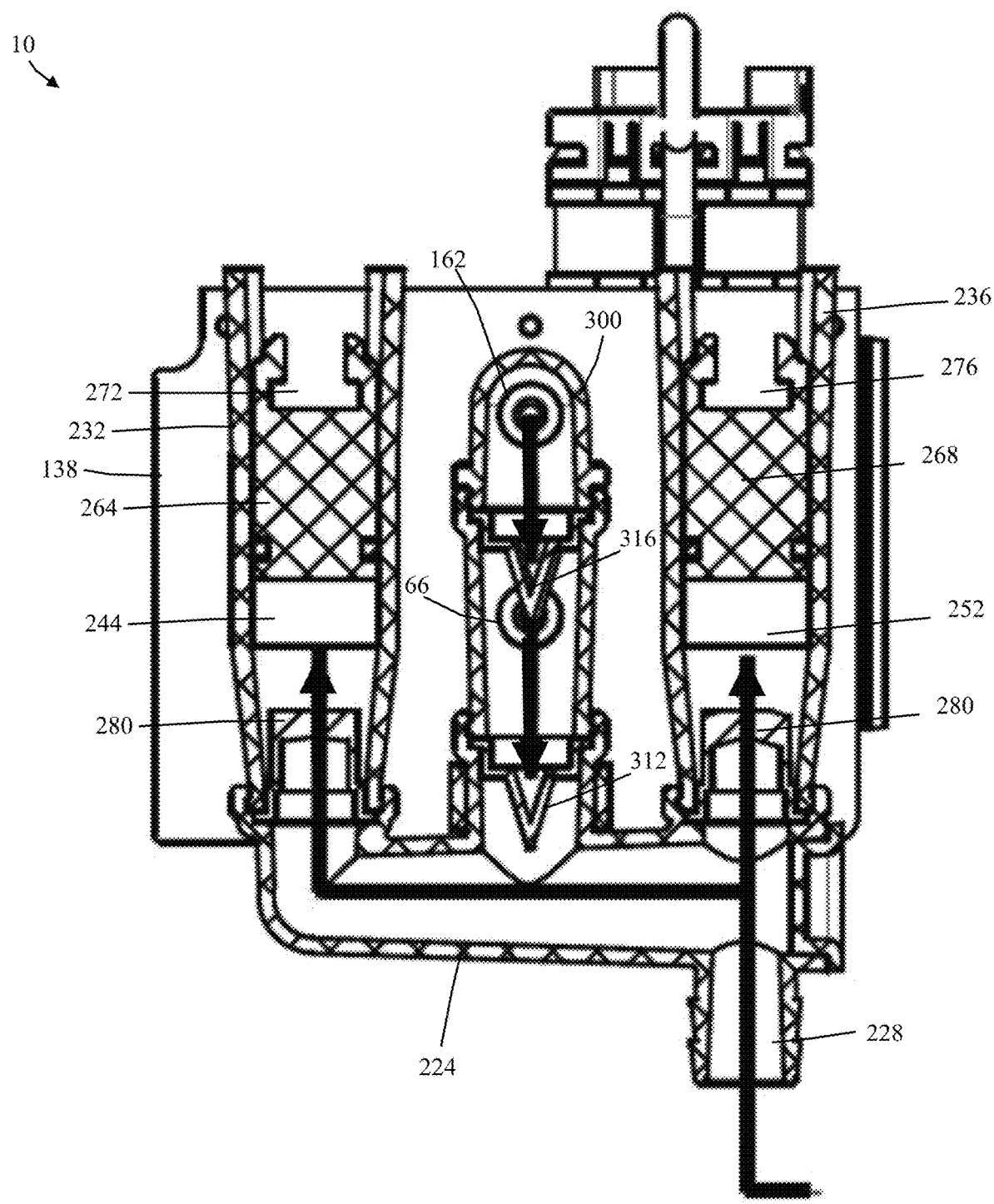
FIG. 14 is a cross-sectional view of the bag device and the regulator.

With continued reference to FIGS. 13 and 14, the bag device 14 includes a first stem 232 coupled to the vacuum connector 224 and a second stem 236 coupled to the vacuum connector 224. In the illustrated embodiment, the first stem 232 includes a first cylinder 240 and at least partially defines a first cavity 244. Likewise, the second stem 236 includes a second cylinder 248 and at least partially defines a second cavity 252. The first cylinder 240 extends along a first cylinder axis 256 and the second cylinder 248 extends along a second cylinder axis 260. In the illustrated embodiment, the second cylinder axis 260 is parallel to the first cylinder axis 256.

A first piston 264 is positioned within the first cylinder 240 and is movable with respect to the first cylinder 240. Likewise, a second piston 268 is positioned within the second cylinder 248 and is movable with respect to the second cylinder 248. As detailed further herein, the pistons 264, 268 are driven to reciprocate within the respective cylinders 240, 248 by the rods 90, 94 of the pump device 14. In the illustrated embodiment, the first piston 264 includes a first notch 272 configured to receive the first flange 98 of the first rod 90, and the second piston 268 includes a second notch 276 configured to receive the second flange 110 of the second rod 94. In the illustrated embodiment, the first cavity 244 is at least partially defined by the first piston 264, and the second cavity 252 is at least partially defined by the second piston 268. As such, the cavities 244, 252 have variable volumes as the pistons 264, 268 reciprocate within the cylinders 240, 248.

With continued reference to FIGS. 13 and 14, the bag device 18 includes a plurality of one-way valves 280. In the illustrated embodiment, a first one-way valve 280 is positioned between the first stem 232 and the vacuum connector 224, and a second one-way valve 280 is positioned between the second stem 236 and the vacuum connector 224.

A first bag port 284 (FIG. 14) extends between the first cavity 244 and the bag 220, and a second bag port 288 extends between the second cavity 252 and the bag 220. The first bag port 284 extends along a first port axis 292, and the first port axis 292 is orthogonal to the first cylinder axis 256. Similarly, the second bag port 288 extends along a second port axis 296, and the second port axis 296 is orthogonal to the second cylinder axis 260.

As detailed further herein, fluid is drawn into the vacuum connector 224 and into the first cavity 244 as the first piston 264 is moving away from the vacuum connector 224 (e.g., as the first piston 264 is retracting). The fluid in the first cavity 244 is then pushed through the first bag port 284 and into the bag 220, as the first piston 264 is moving toward the vacuum connector 224 (e.g., as the first piston 264 is extending). As the first piston 264 is moving towards the vacuum connector 224, the first one-way valve 280 positioned between the first stem 232 and the vacuum connector 224 prevents the fluid in the first cavity 244 from reentering the vacuum connector 224. Similarly, fluid is drawn into the second cavity 252 as the second piston 268 is moving away from the vacuum connector 224 and expelled into the bag 220 through the second bag port 288 as the second piston 268 moves towards the vacuum connector 224. In some embodiments, the first piston 264 and the second piston 268 are driven out of phase with each other (e.g., alternating) such that one piston is drawing fluid in as the other piston is expelling fluid into the bag. In the illustrated embodiment, the bag device 18 forms a fluid transfer pump. In some embodiments, the fluid being transferred is a biological fluid (e.g., vomit, blood, mucus, etc.) from a patient. In some embodiments, the fluid is a liquid containing semi-solids or solids.

In the illustrated embodiment, the bag device 18 further includes a regulator stem assembly 300 coupled to the vacuum connector 224. In the illustrated embodiment, the regulator stem assembly 300 includes a first aperture 304 (corresponding to the first port 162 on the pump device 14) and a second aperture 308 (corresponding to the second port 166 on the pump device 14). In some embodiments, the regulator stem assembly 300 includes a first one-way valve 312 at the interface with the vacuum connector 224 and a second one-way valve 316 positioned between the apertures 304, 308. As detailed herein, the second aperture 308 leads to the sensing chamber 174, and the first aperture 304 leads to the cavity 154 in the pressure regulator 138.

Figure 15:
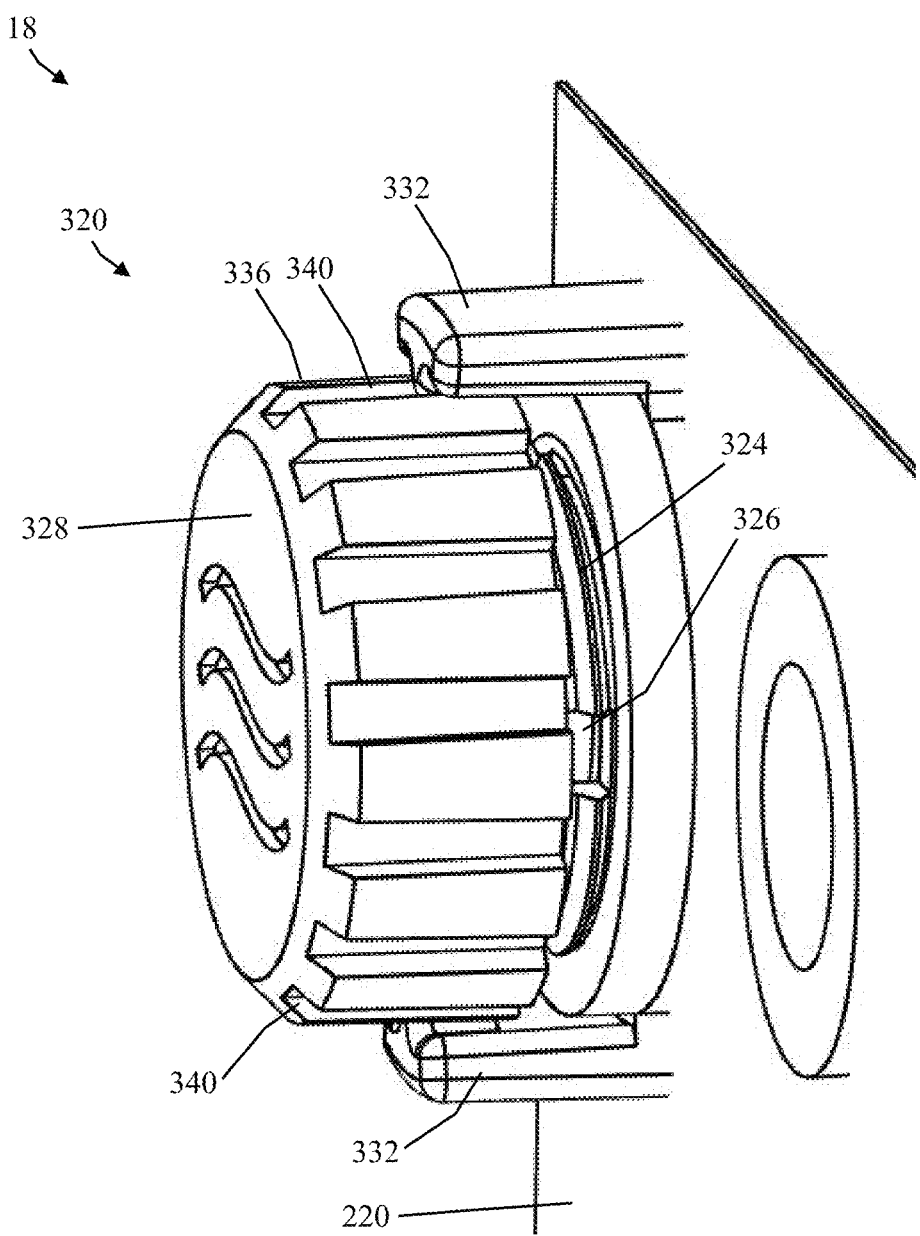
FIG. 15 is a perspective view of a cap assembly on the bag device of FIG. 1.

With reference to FIG. 15, the bag device 18 includes a cap assembly 320 with a thread portion 324 with at least one vent 326, a cap 328, and a ratchet 332. In the illustrated embodiment, the cap assembly 320 is movable between a vent position, a closed position, and a removed position. In the vent position, the vents 326 are exposed to atmosphere. In a closed position, the vents 326 are removed blocked by the cap 328. In a removed position, the cap 328 is separated from the thread portion 324. In some embodiment, the cap assembly 320 is initially in a vent position. An outer surface 336 of the cap 328 includes a plurality of grooves 340 that interface with the ratchet 332. The ratchet 332 acts as a detent to secure the cap 328 is position when the cap 328 is not being rotated by a user.

Figure 16:
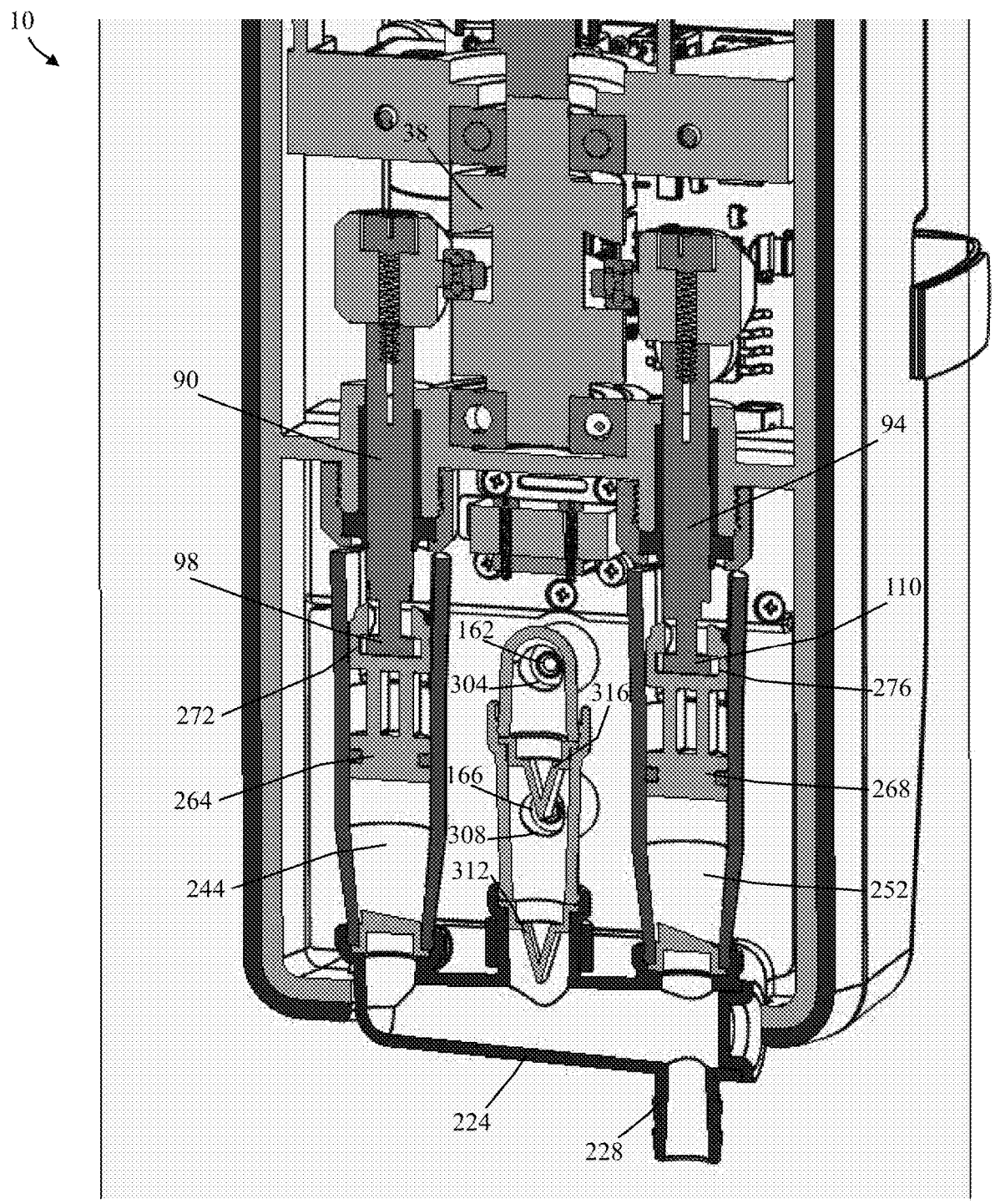
FIG. 16 is a partial perspective cross-sectional view of the bag device coupled to the pump device of FIG. 1.
Figure 17:
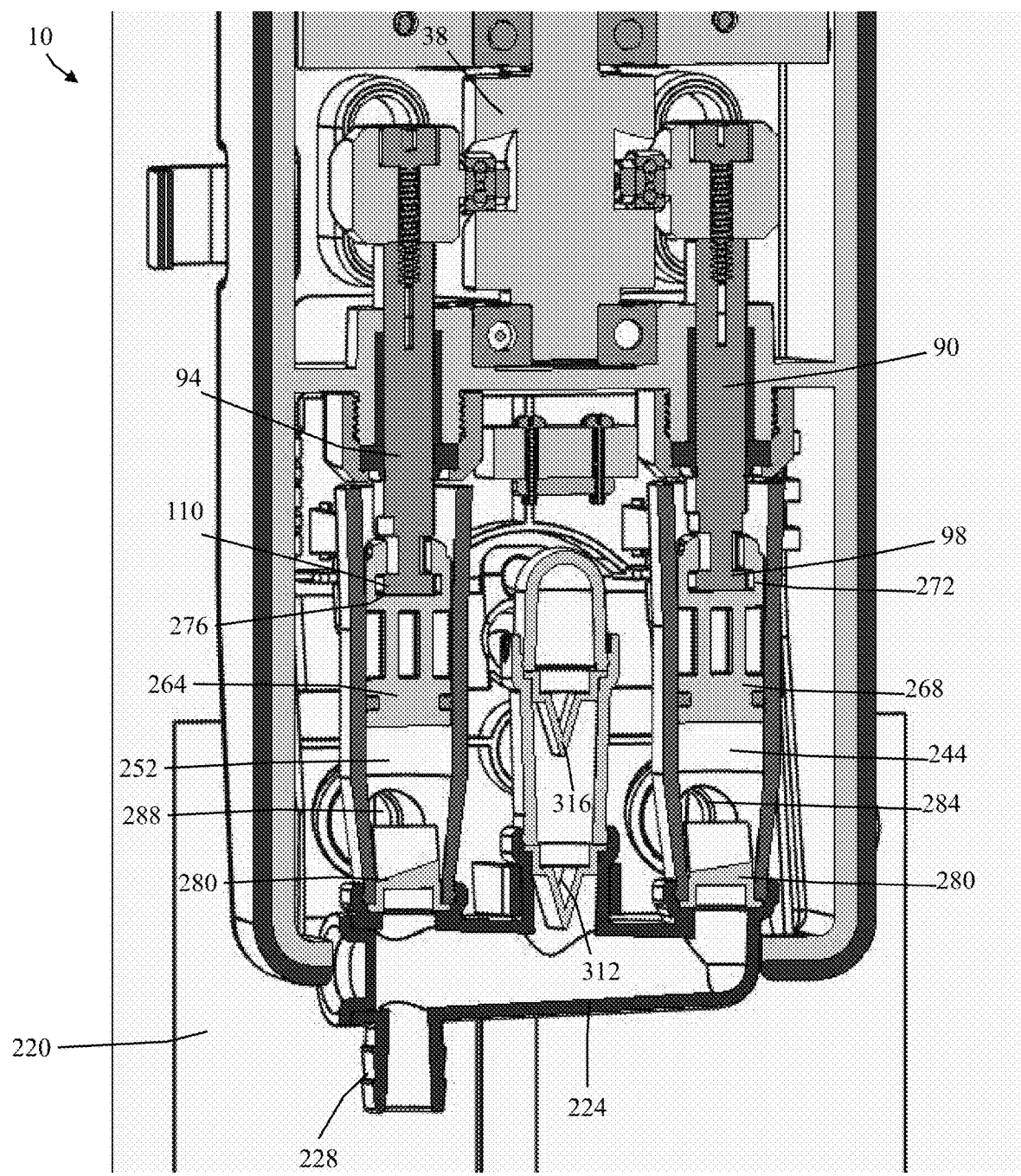
FIG. 17 is another partial perspective cross-sectional view of the bag device coupled to the pump device of FIG. 1.

With reference to FIGS. 16 and 17, the bag device 18 is shown attached to the pump device 14. The end 102 of the first rod 90 is received within the notch 272 of the first piston 264 and the end 114 of the second rod 94 is received within the notch 276 of the second piston 268. The pump device 14 is shown in FIGS. 16 and 17 in the parked configuration such that the bag device 18 may be easily removed or attached, as desired.

Figure 18:
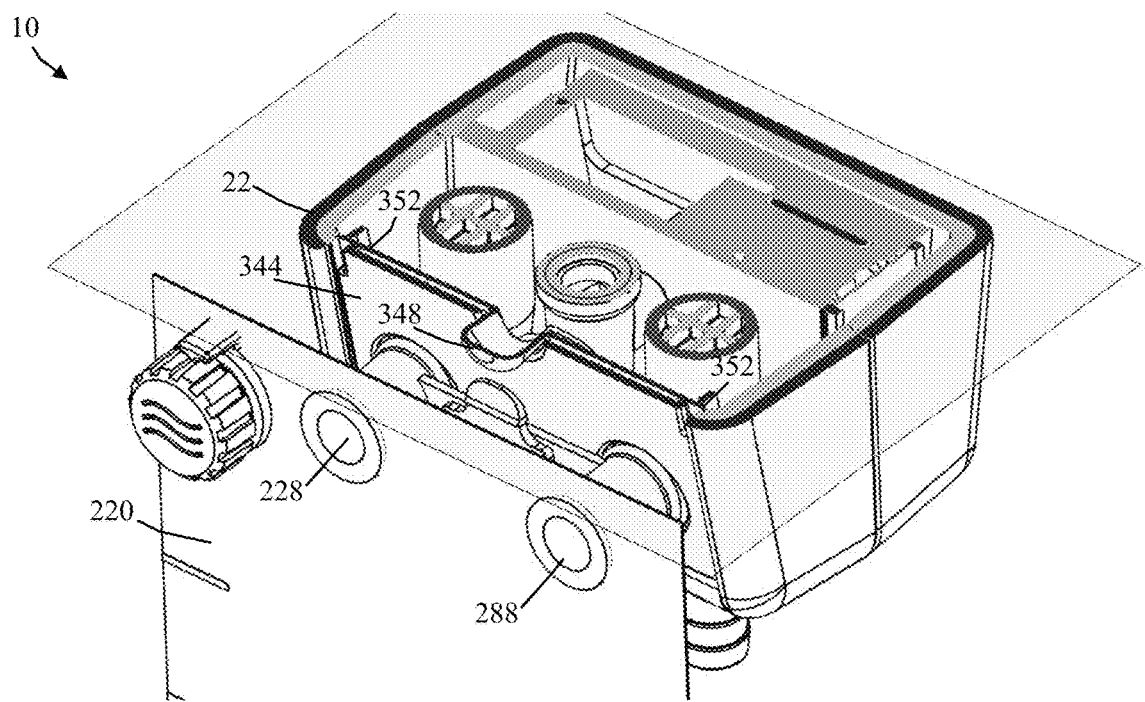
FIG. 18 is another partial perspective cross-sectional view of the bag device coupled to the pump device of FIG. 1.
Figure 19:
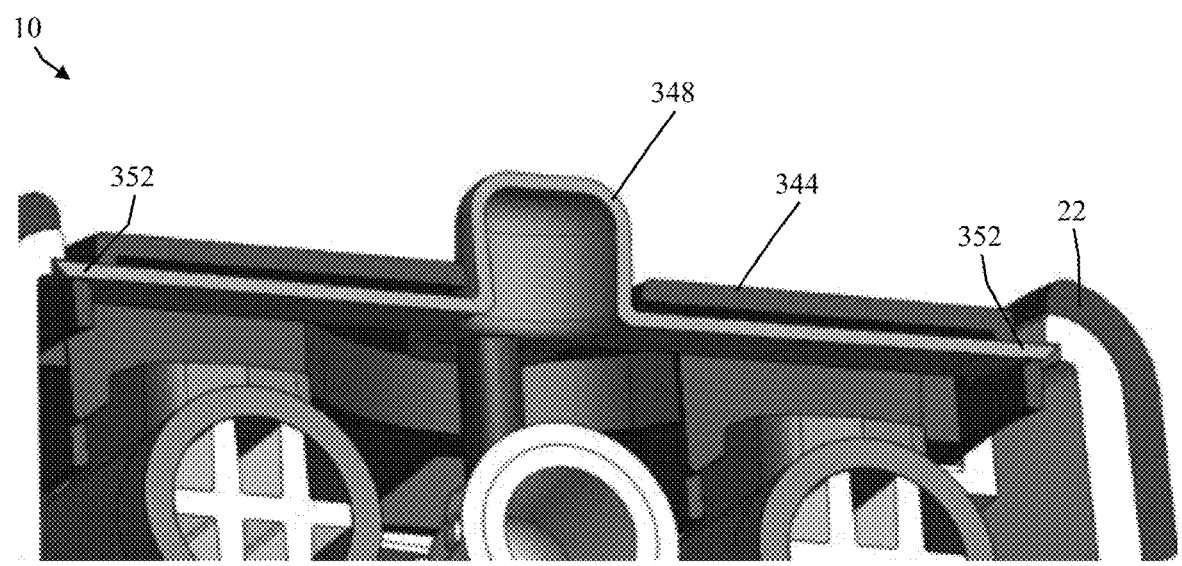
FIG. 19 is another partial perspective cross-sectional view of the bag device coupled to the pump device of FIG. 1.

With reference to FIGS. 18 and 19, the bag device 18 further includes a cover 344 and an actuator 348. In the illustrated embodiment, at least a portion of the actuator 348 extends from the cover 344 (e.g., a user actuated portion). When the actuator 348 is not depressed by a user, wings 352 on the actuator 348 interface with the pump device 14 to secure the bag device 18 in position. When the actuator 348 is depressed, the actuator 348 deflects and the wings 352 are retracted away from the pump device 14 to free the bag device 18 from the pump device 14. In the illustrated embodiment, the actuator 348 deflects in response to activation by a user.

Figure 22:
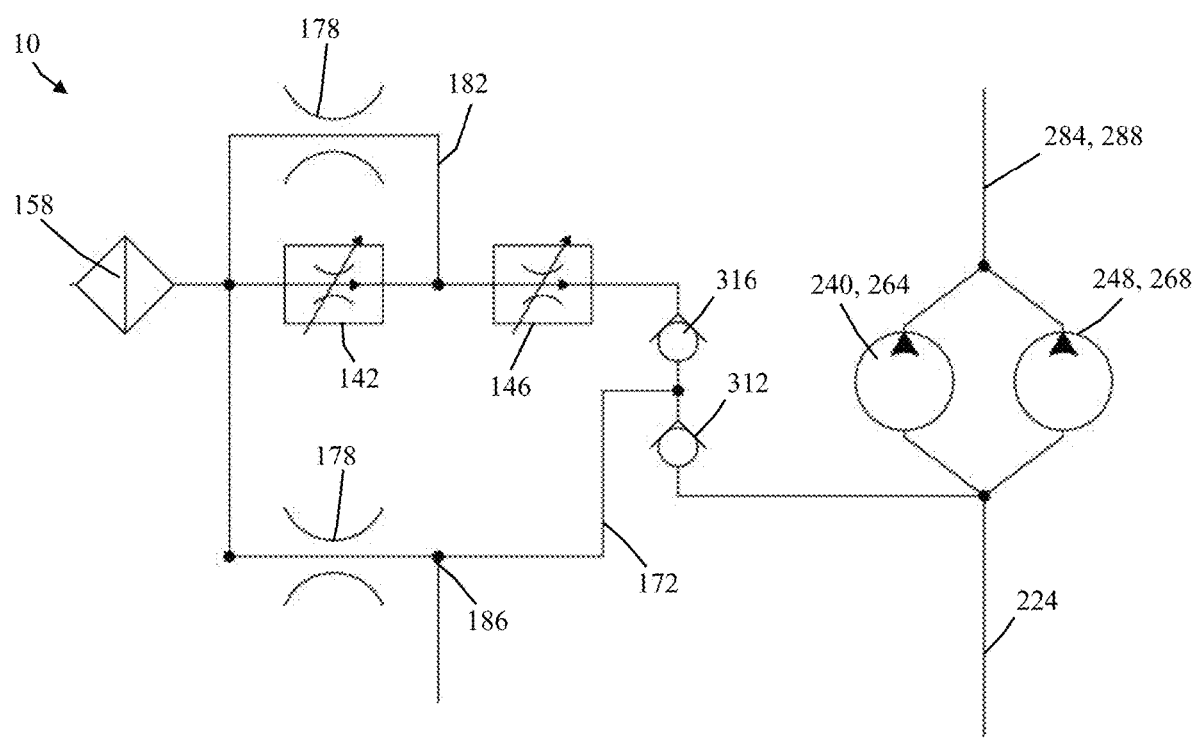
FIG. 22 is a pneumatic schematic of the airflow of the system of FIG. 1.

With reference to FIG. 22, the pneumatic schematic for the system 10 is illustrated.

The system 10 disclosed herein solves the problems associated with using stop-gap measures for suction in the field which have led to compromise in patient care. Deficient care results from insufficient amount of suction, incomplete suction as the devices and systems simply run out of adequate power, and capturing so much first responder attention that other, serious injuries remain inadequately treated. The system 10 disclosed herein provides long-term, sufficiently powered, appropriate suction strength in a miniaturized system novel to the industry. As detailed herein, the system 10 is portable. In some embodiments, the system 10 measures approximately 7.58" in height, 3.25" in width, and 2.5" in depth. In some embodiments, the system 10 is utilized for airway suction in airway procedures including Cricothyroidotomy and intubation; chest suction for management of penetrating chest trauma (e.g., with 20 mmHg continuous or intermittent suction); or enroute damage control surgery suction for open thoracotomy procedures by Advanced Resuscitative Surgical teams.

In some embodiments, the system 10 provides an adjustable suction pressure within a range of approximately 0 mmHg to approximately 550 mmHg. In some embodiments, the system 10 provides an adjustable suction pressure within a range of approximately 0 mmHg to approximately 750 mm Hg. In some embodiments, the system 10 runs at approximately 80 mmHg for approximately two hours, which accounts for procedures such as in transition DCS applications. In some embodiments, the system 10 runs at approximately 20 mmHg (approximately 30 cmH20) for an in transition chest injury management procedure, for example.

One skilled in the art will readily appreciate that the present disclosure is well adapted to carry out the objects and obtain the ends and advantages mentioned, as well as those inherent herein. The present disclosure described herein are exemplary embodiments and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Various features and advantages are set forth in the following claims.

What is claimed is:

1. A device comprising:
a housing defining a recess;
a motor assembly;
a barrel drive positioned within the housing and rotatably driven by the motor assembly about a barrel axis; wherein a cam is formed in the barrel drive;
a first follower positioned within the cam;
a second follower positioned within the cam;
a first rod coupled to the first follower;
a second rod coupled to the second follower; wherein the first rod and the second rod are at least partially positioned within the recess;
a pressure sensor;
a pressure regulator including a cavity, an air inlet, a first port in fluid communication with the cavity by a first passageway, and a second port in fluid communication with the pressure sensor by a second passageway; and
a valve in fluid communication with the cavity; wherein the valve selectively communicates the cavity with ambient air from the air inlet to adjust a pressure within the cavity.

2. The device of claim 1, wherein operation of the motor assembly is adjusted in response to detecting a pressure in the cavity with the pressure sensor.

3. The device of claim 1, wherein operation of the valve is adjusted in response to detecting the pressure in the cavity with the pressure sensor.

4. The device of claim 1, further including a processor electrically coupled to the motor assembly, the pressure sensor, and the valve.

5. The device of claim 1, wherein the motor assembly includes an electric motor, a gear set, a transmission, a first position sensor, and a second position sensor.

6. The device of claim 1, wherein the barrel drive includes an outer cylindrical surface, and the cam is formed in the outer cylindrical surface of the barrel drive.

7. The device of claim 6, wherein the cam extends 360 degrees around the outer cylindrical surface.

8. The device of claim 1, wherein the first rod defines a first rod axis, and the second rod defines a second rod axis, and wherein the first rod axis is parallel to the second rod axis.

9. The device of claim 8, wherein the first rod axis is parallel to the barrel axis.

10. The device of claim 1, further including a first seal and a second seal, wherein the first rod extends through the first seal and is movable with respect to the first seal, and the second rod extends through the second seal and is movable with respect to the second seal.

11. The device of claim 1, wherein the first rod includes a flange formed at an end of the first rod, and wherein the first rod includes a groove that at least partially defines the flange.

12. The device of claim 1, wherein the air inlet is in fluid communication with the cavity by a third passageway including a metered insert.

13. The device of claim 12, wherein the pressure regulator further includes a fourth passageway that extends between the air inlet and the pressure sensor.

14. The device of claim 1, further including a sensor, configured to detect the presence of an attachment, positioned within the recess.

15. The device of claim 1, further including a status display and a user interface, wherein the pressure in the cavity is adjustable in response to receiving a user input at the user interface.

16. The device of claim 1, further including a battery assembly, and wherein the battery assembly is removable.

17. The device of claim 1, further including a latch with a plurality of teeth, a spring biasing the latch into a closed position, and wherein the housing includes a cover with a plurality of teeth engaged with the plurality of teeth on the latch, and wherein the cover is moveable in response to the latch moved against the spring bias into an open position.

18. The device of claim 1, wherein the first rod is driven out of phase with the second rod.

19. The device of claim 1, wherein the first rod includes a flange formed at an end of the first rod, and wherein the flange is positioned within the recess.

20. The device of claim 1, wherein the first port is at least partially positioned within the recess; and the second port is at least partially positioned within the recess.

21. The device of claim 18, wherein the device is placed in a parked configuration in response to deenergizing the device, wherein the parked configuration includes the first rod and the second rod at the same longitudinal position along the barrel axis.

22. The device of claim 21, wherein the motor assembly includes a first position sensor; and wherein the device is placed in the parked configuration based on feedback from the first position sensor.

* * * * *